(12) United States Patent
Doane et al.

(10) Patent No.: US 12,213,467 B2
(45) Date of Patent: Feb. 4, 2025

(54) APPARATUS AND METHOD FOR BREEDING BLACK SOLDIER FLIES

(71) Applicant: Oberland Agriscience Inc., Halifax (CA)

(72) Inventors: Nicholas Peter Frank Doane, Halifax (CA); Gregory Patrick Wanger, Halifax (CA)

(73) Assignee: Oberland Agriscience Inc., Halifax (CA)

( * ) Notice: Subject to any disclaimer, the term of this patent is extended or adjusted under 35 U.S.C. 154(b) by 62 days.

(21) Appl. No.: 17/957,741

(22) Filed: Sep. 30, 2022

(65) Prior Publication Data

US 2023/0022621 A1    Jan. 26, 2023

Related U.S. Application Data

(63) Continuation of application No. PCT/CA2021/050436, filed on Mar. 31, 2021.

(Continued)

(51) Int. Cl.
*A01K 67/033* (2006.01)

(52) U.S. Cl.
CPC ...... *A01K 67/033* (2013.01); *A01K 2227/706* (2013.01)

(58) Field of Classification Search
CPC ................... A01K 67/033; A01K 2227/706
See application file for complete search history.

(56) References Cited

U.S. PATENT DOCUMENTS 9,510,572 B2 * 12/2016 Aldana ............... A01K 67/033
11,470,829 B2 * 10/2022 Józefiak .............. A01K 67/033
(Continued)

FOREIGN PATENT DOCUMENTS

FR           3013561 A1      5/2015
WO    WO-2013166590 A1 * 11/2013  ........... A01K 67/033
(Continued)

OTHER PUBLICATIONS

International Search Report and Written Opinion mailed Jul. 2, 2021 in International Patent Application No. PCT/CA2021/050436 (9 pages).

(Continued)

*Primary Examiner* — Monica L Perry
*Assistant Examiner* — Aaron M Rodziwicz
(74) *Attorney, Agent, or Firm* — SMART & BIGGAR LP; Tonino Rosario Orsi; Justin Philpott

(57) ABSTRACT

An apparatus and method of Black Soldier Fly breeding are provided. The method includes emitting a lure light to lure Black Soldier Flies into an interior space of a fly enclosure, emitting a mating light to induce Black Soldier Flies in the interior space to mate, and illuminating the interior space to a first illuminance above an ovipositing illuminance threshold and below a mating inducing illuminance threshold. The lure light has a first wavelength range that attracts recently hatched Black Soldier Flies into the fly enclosure through one or more lure ports formed in the fly enclosure. The mating light has a second wavelength range that induces Black Soldier Flies to mate. The method may also include illuminating the interior space to a second illuminance below the ovipositing illuminance threshold so that Black Soldier Flies in the interior space are encouraged to rest.

29 Claims, 6 Drawing Sheets

Related U.S. Application Data

(60) Provisional application No. 63/003,557, filed on Apr. 1, 2020.

(56) References Cited

U.S. PATENT DOCUMENTS

| | | | |
|---|---|---|---|
| 2008/0134568 A1* | 6/2008 | Cowan | A01M 1/04 424/84 |
| 2009/0000553 A1* | 1/2009 | Ramos Elorduy Y Blasquez | A01K 67/033 119/6.5 |
| 2014/0020630 A1* | 1/2014 | Courtright | A01K 67/033 119/6.6 |
| 2018/0070566 A1* | 3/2018 | Comparat | A01K 67/033 |

FOREIGN PATENT DOCUMENTS

| | | |
|---|---|---|
| WO | 2017/072715 A1 | 5/2017 |
| WO | 2018/186741 A1 | 10/2018 |
| WO | 2019/125162 A8 | 6/2019 |
| WO | 2019/154563 A1 | 8/2019 |

OTHER PUBLICATIONS

Sheppard et al., "Rearing Methods for the Black Soldier Fly (Diptera: Stratiomyidae)," Journal of Medical Entomology, 2002, 39(4): 695-698.

Hoc et al., "Optimization of black soldier fly (*Hermetia illucens*) artificial reproduction," PLoS ONE, 2019, 14(4): E0216160, pp. 1-13.

Insect.Systems BV website, accessed Jan. 14, 2020 <https://www.insect.systems>.

Liu et al., "Mating success of the black soldier fly, *Hermetia illucens* (Diptera: Stratiomyidae), under four artificial light sources," Journal of Photochemistry & Photobiology; B: Biology, Apr. 2020 (epub Feb. 5, 2020), 205: 111815.

\* cited by examiner

APPARATUS AND METHOD FOR BREEDING BLACK SOLDIER FLIES

CROSS-REFERENCE TO RELATED APPLICATION

This application is a continuation of International Patent Application No. PCT/CA2021/050436 filed Mar. 31, 2021, which claims the benefit of U.S. Provisional Patent Application No. 63/003,557 filed Apr. 1, 2020, and the entire contents of each are hereby incorporated by reference.

FIELD

This application generally relates to the breeding of insects, and more specifically to an apparatus and method for breeding *Hermetia illucens* (commonly referred to as the Black Soldier Fly).

BACKGROUND

Market trends, a growing body of scientific literature and several large-scale feed trials have revealed that reared insects are an attractive and sustainable alternate source of protein. The high protein content of such insects (e.g., about 30-50% protein by mass) make them an excellent food source for fish, reptiles, and livestock. Compared to other sources of protein, e.g., corn, cattle and soy, insects offer a sizable increase in protein yield per hectare. Not only are insects an excellent source of protein, they are also incredibly efficient at converting food wastes into biomass. Of the insects that may serve as a source of protein, *Hermetia illucens* (Black Soldier Flies) have been shown to offer a wide range of advantages.

SUMMARY

In a broad aspect, at least one embodiment described herein provides an apparatus for breeding Black Soldier Flies. The apparatus may include a fly enclosure defining an interior fly space, one or more lure lighting devices, and one or more mating lighting devices. The fly enclosure may have at least one lure port. Each lure lighting device may be operable to emit lure light having a first wavelength range that attracts the Black Soldier Flies through the at least one lure port into the interior fly space. Each lure lighting device may be spaced apart from the at least one lure port and oriented so that the lure light emitted by that lure lighting device is visible through the at least one lure port. Each mating lighting device may be operable to emit mating light having a second wavelength range that induces the Black Soldier Flies in the interior fly space to mate. Each mating lighting device may be oriented so that the mating light emitted by that mate lighting device illuminates the interior fly space.

In at least one embodiment, the apparatus may also include one or more base lighting devices, each base lighting device may be operable to emit a base light, and each base lighting device may be oriented so that a collective base light emitted by the one or more base lighting devices illuminates the interior fly space to an illuminance above an ovipositing illuminance threshold.

In at least one embodiment, the illuminance may be above the ovipositing illuminance threshold and below 1500 lux.

In at least one embodiment, the ovipositing illuminance threshold may be between about 1 to about 6 lux.

In at least one embodiment, the first wavelength range may have a lower limit of about 280 nanometers and an upper limit of about 400 nanometers.

In at least one embodiment, the first wavelength range may be substantially between about 350 nanometers and about 400 nanometers.

In at least one embodiment, the second wavelength range may have a lower limit of about 380 nanometers and an upper limit of about 740 nanometers.

In at least one embodiment, the second wavelength range may be substantially between about 410 nanometers and about 730 nanometers.

In at least one embodiment, each mating lighting device may include about 410, about 430 to about 440, about 450 to about 475, about 620 to about 630, about 650 to about 660 and about 730 nanometer light-emitting diodes.

In at least one embodiment, each lure lighting device may be spaced about 0.5 to 2.5 meters apart from the at least one lure port.

In at least one embodiment, each base lighting device may be positioned outside and above the fly enclosure.

In at least one embodiment, each base lighting device may be positioned within the fly enclosure.

In at least one embodiment, each base lighting device may be positioned between about 20 to about 100 centimeters above or below the one or more mating lighting devices.

In at least one embodiment, each lure lighting device may be positioned within the fly enclosure.

In at least one embodiment, each mating lighting device may be positioned outside and above the fly enclosure.

In at least one embodiment, each mating lighting device may be located within the fly enclosure at an upper portion of the interior fly space.

In at least one embodiment, the apparatus may also include one or more egg-laying regions located within the fly enclosure.

In at least one embodiment, each egg-laying region may include an egg block on which gravid Black Soldier Flies lay eggs and an attractant substance to attract the gravid Black Soldier Flies to the egg block.

In at least one embodiment, the fly enclosure may be at least partially formed from a mesh material.

In at least one embodiment, the apparatus may also include at least one pupae cartridge, the at least one pupae cartridge may be configured for holding a plurality of Black Soldier Fly pupae, and the at least one pupae cartridge may be coupled to the at least one lure port.

In at least one embodiment, the at least one lure port may include a frustoconical conduit connected thereto, and the frustoconical conduit may be adapted to allow for passage of hatched Black Soldier Flies from the at least one pupae cartridge into the interior fly space, while restricting passage of the Black Soldier Flies from the interior fly space to the at least one pupae cartridge.

In at least one embodiment, the frustoconical conduit may include a plurality of perforations to allow for passage of the lure light from the one or more lure lighting devices to the at least one lure port.

In at least one embodiment, there may be a plurality of pupae cartridges, a plurality of lure ports, and each pupae cartridge may be coupled to a corresponding one of the lure ports.

In at least one embodiment, the at least one pupae cartridge may include a see-through material to allow visual inspection of the plurality of Black Soldier Fly pupae held therein.

In at least one embodiment, the apparatus may also include a pupae cartridge enclosure adjacent the fly enclosure, the pupae cartridge enclosure may be structured to define an interior cartridge space, one of the fly enclosure and the pupae cartridge enclosure may include a dividing wall that separates the interior fly space from the interior cartridge space, and the dividing wall may include the at least one lure port.

In at least one embodiment, the dividing wall may be substantially impervious to light.

In at least one embodiment, the pupae cartridge enclosure may be substantially impervious to light.

In at least one embodiment, at least one of the lure lighting devices may include a tube light that is oriented so that it is substantially parallel to the dividing wall.

In at least one embodiment, the fly enclosure may have a bottom side that is funnel-shaped to collect deceased Black Soldier Flies under gravity.

In at least one embodiment, the fly enclosure may have at least one access port to permit removal of deceased Black Soldier Flies from the interior fly space.

In at least one embodiment, the fly enclosure may include a vacuum port located at the bottom side.

In at least one embodiment, the fly enclosure may have a sealable opening to permit removal of Black Soldier Fly eggs from the interior fly space.

In at least one embodiment, the apparatus may also include one or more contrast panels, and each contrast panel may be positioned above the fly enclosure.

In at least one embodiment, the apparatus may also include a controller having at least one processor that is operable to receive program instructions from a memory device, and the controller may be coupled to one or more of (i) each lure lighting device and (ii) each mating lighting device so that when the at least one processor executes the program instructions the controller is configured to control the activation of at least one of the lure lighting devices and/or (ii) at least one of the mating lighting devices in an automated fashion.

In at least one embodiment, the controller may be configured to control one or more of (i) at least one of the lure lighting devices and/or (ii) at least one of the mating lighting devices according to a lighting schedule.

In at least one embodiment, the controller may be configured to activate at least one of the mating lighting devices for a mating period after a luring period for which at least one of the lure lighting devices is activated.

In at least one embodiment, the controller may be configured to activate at least one of the mating lighting devices immediately after the luring period.

In at least one embodiment, the controller may be configured to activate at least one of the mating lighting devices for a mating period during a later portion of the luring period for which at least one of the lure lighting devices is activated.

In at least one embodiment, the controller may be configured to activate at least one of the lure lighting devices so that the luring period lasts for about 30 minutes to about 90 minutes.

In at least one embodiment, the controller may be configured to activate at least one of the mating lighting devices so that the mating period lasts for about 2 hours to about 4 hours.

In at least one embodiment, the controller may be coupled to each of the base lighting devices so that when the at one processor executes the program instructions the controller is configured to control the activation of at least one of the base lighting devices in an automated fashion, and the controller may be configured to activate at least one of the base lighting devices for an ovipositing period after the mating period for which at least one of the mating lighting devices is activated.

In at least one embodiment, the controller may be configured to activate at least one of the base lighting devices so that the ovipositing period lasts for about 6 to 12 hours.

In another aspect, at least one embodiment described herein provides a method of breeding Black Soldier Flies. The method may include emitting lure light to lure the Black Soldier Flies into an interior fly space of a fly enclosure, emitting mating light to induce the Black Soldier Flies in the interior fly space to mate, and illuminating the interior fly space to a first illuminance above an ovipositing illuminance threshold and below a mating inducing illuminance threshold. The lure light may have a first wavelength range that attracts the Black Soldier Flies. The mating light may have a second wavelength range that induces the Black Soldier Flies to mate.

In at least one embodiment, the method may further include illuminating the interior fly space to a second illuminance below the ovipositing illuminance threshold so that the Black Soldier Flies in the interior fly space are encouraged to rest.

In at least one embodiment, the method may further include introducing at least one pupae cartridge so that it is coupled with the interior fly space of the fly enclosure, the at least one pupae cartridge may hold a plurality of Black Soldier Fly pupae, and emitting the lure light may further include luring the Black Soldier Flies that have hatched from the plurality of Black Soldier Fly pupae into the interior fly space.

In at least one embodiment, introducing the at least one pupae cartridge may include keeping the at least one pupae cartridge coupled with the interior fly space of the fly enclosure for a hatching period of about 7 to 12 days.

In at least one embodiment, there are a plurality of pupae cartridges, and introducing the at least one pupae cartridge may include replacing one of the plurality of pupae cartridges about every 2 to 3 days.

In at least one embodiment, the at least one pupae cartridge may be coupled with the interior fly space, at least in part, by one or more lure ports, and emitting the lure light may include emitting the lure light so that it is visible through each lure port.

In at least one embodiment, the method may include emitting the mating light after emitting the lure light.

In at least one embodiment, the method may include emitting the mating light immediately after emitting the lure light.

In at least one embodiment, the method may include starting to emit the mating light during a later portion of emitting the lure light.

In at least one embodiment, the method may include illuminating the interior fly space to the first illuminance after emitting the mating light.

In at least one embodiment, the method may include illuminating the interior fly space to the first illuminance immediately after emitting the mating light.

In at least one embodiment, the method may include starting to emit the lure light during a portion of illuminating the interior fly space to the first illuminance.

In at least one embodiment, the method may include emitting the lure light for a luring period of about 30 minutes to about 90 minutes.

In at least one embodiment, the method may include emitting the mating light for a mating period of about 2 hours to about 4 hours.

In at least one embodiment, the method may include illuminating the interior fly space to the first illuminance for an ovipositing period of about 6 hours to about 12 hours.

In at least one embodiment, the method may include illuminating the interior fly space to the second illuminance for an inactive period of about 6 hours to about 12 hours.

In at least one embodiment, the ovipositing illuminance threshold may be about 1 to about 6 lux, and the mating inducing illuminance threshold may be about 1500 lux.

In at least one embodiment, emitting the mating light may include using at least one contrast panel to help male Black Soldier Flies see and engage female Black Soldier Flies flying overhead.

In at least one embodiment, the method may also include emitting the lure light by activating one or more lure lighting devices.

In at least one embodiment, the method may also include emitting the mating light by activating one or more mating lighting devices.

In at least one embodiment, illuminating the interior fly space to the first illuminance may include providing a base light by (i) activating one or more base lighting devices, (ii) allowing sunlight to enter the interior fly space, or (iii) a combination of (i) and (ii).

In at least one embodiment, the method may also include using a controller having at least one processor to control at least one of the lighting devices to emit light, and the controller may be configured operate according to a lighting schedule.

In at least one embodiment, the method may also include illuminating the interior fly space to the second illuminance by removing or blocking all sources of light proximate to the fly enclosure.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

Figure 1:
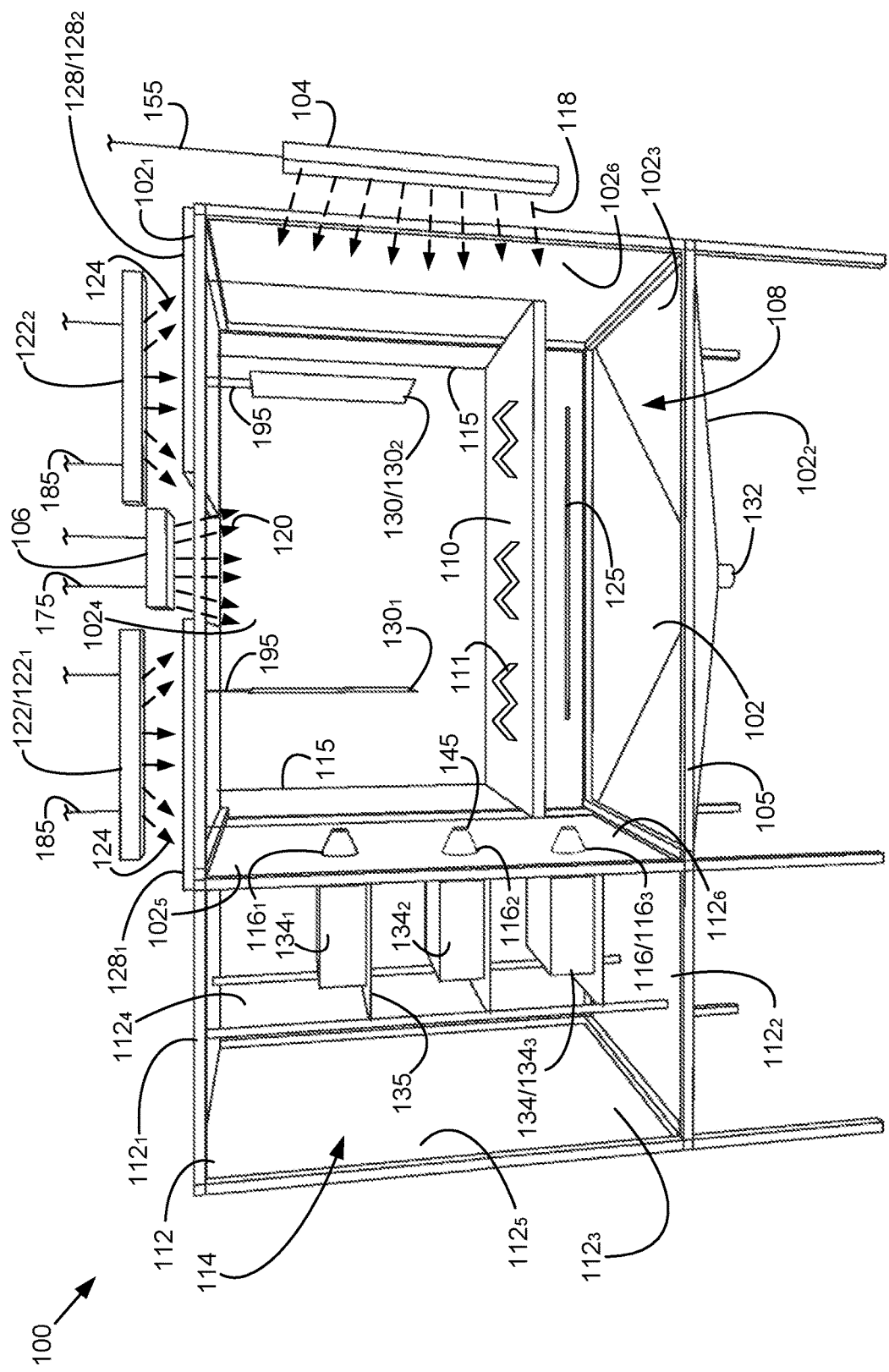
FIG. 1 is a front view of an apparatus for breeding Black Soldier Flies, in accordance with a first example embodiment.

Further aspects and features of the example embodiments described herein will appear from the following description taken together with the accompanying drawings.

DETAILED DESCRIPTION

Various embodiments in accordance with the teachings herein will be described below to provide an example of at least one embodiment of the claimed subject matter. No embodiment described herein limits any claimed subject matter. The claimed subject matter is not limited to devices, systems or methods having all of the features of any one of the devices, systems or methods described below or to features common to multiple or all of the devices, systems or methods described herein. It is possible that there may be a device, system or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, optical or electrical connotation. For example, as used herein, the terms coupled or coupling can indicate that two elements or devices can be directly connected to one another or connected to one another through one or more intermediate elements or devices via an electrical signal, an electrical connection, a mechanical element, an optical element, or a light pathway depending on the particular context.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term, such as by 1%, 2%, 5% or 10%, for example, if this deviation does not negate the meaning of the term it modifies. For example, the expression "about 300 nanometers" means 300 nanometers+/−10% (between 270 and 330 nanometers).

Furthermore, the recitation of numerical ranges by endpoints herein includes all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5%, or 10%, for example.

The terms "an embodiment", "embodiment", "embodiments", "the embodiment", "the embodiments", "one or more embodiments", "some embodiments", "at least one embodiment", and "one embodiment" mean one or more (but not all) embodiments of the claimed subject matter, unless expressly specified otherwise.

The terms "including", "comprising", and variations thereof mean "including but not limited to", unless expressly specified otherwise. A listing of items does not imply that any or all of the items are mutually exclusive, unless expressly specified otherwise. The terms "a", "an", and "the" mean "one or more", unless expressly specified otherwise.

In at least one example embodiment of the devices, systems, or methods described in accordance with the teachings herein, a combination of hardware and software may be used for implementation. For example, at least one of the embodiments described herein may be implemented, at least in part, by using one or more computer programs, executing on one or more programmable devices, such as a controller, comprising at least one processing element and at least one storage element (i.e., at least one volatile memory element and at least one non-volatile memory element). The hardware may comprise input devices including at least one of a touch screen, a keyboard, a mouse, buttons, keys, sliders, and the like, as well as one or more of a display, a printer, one or more sensors, and the like depending on the implementation of the hardware.

It should also be noted that some elements that are used to implement at least part of at least one of the embodiments described herein may be implemented via software that is written in a high-level procedural language such as object-oriented programming. The program code may be written in C++, C#, JavaScript, Python, or any other suitable programming language and may comprise modules or classes, as is known to those skilled in object-oriented programming. Alternatively, or in addition thereto, some of these elements implemented via software may be written in assembly language, machine language, or firmware as needed. In either case, the language may be a compiled or interpreted language.

At least some of these software programs may be stored on a computer readable medium such as, but not limited to, a ROM, a magnetic disk, an optical disc, a USB key, and the like that is readable by a device having a processor, an operating system, and the associated hardware and software that is necessary to implement the functionality of at least one of the embodiments described herein. The software program code, when read by the device, configures the device to operate in a new, specific, and predefined manner (e.g., as a specific-purpose computer) in order to perform at least one of the methods described herein.

At least some of the programs associated with the devices, systems, and methods of the embodiments described herein may be capable of being distributed in a computer program product comprising a computer readable medium that bears computer usable instructions, such as program code, for one or more processing units. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g., downloads), media, digital and analog signals, and the like. The computer useable instructions may also be in various formats, including compiled and non-compiled code.

In addition, some elements herein may be identified by a part number, which is composed of a base number followed by an alphabetical or subscript-numerical suffix (e.g., 116$a$, or 116$_1$). Multiple elements herein may be identified by part numbers that share a base number in common and that differ by their suffixes (e.g., 116$_1$, 116$_2$, and 116$_3$). All elements with a common base number may be referred to collectively or generically using the base number without a suffix (e.g., 116).

Insects are quickly becoming an important protein source to meet increasing global demand. When compared to the insects commonly used as a protein source, Black Soldier Flies offer numerous advantages. Black Soldier Flies are a non-invasive, non-pathogenic, non-biting species with an excellent nutrient profile. Black Soldier Flies are also a highly resilient and adaptable sub-tropical species.

As a member of the Family Stratiomyidae, the Black Soldier Fly goes through full metamorphosis during their lifespan. This includes egg, larval, pupae and adult life cycle stages. Larvae will hatch from the egg stage after 48-72 hours. Black Soldier Fly larvae eat decomposing organics. Consequently, they present no threat to growing crops or livestock. The larvae are incredibly efficient at converting organic waste into biomass (up to 25% wet weight conversion), making them ideal for bioconversion of organic waste. Not only are they highly efficient, Black Soldier Fly larvae also rapidly convert organic waste into high biomass.

The yield of protein per hectare for Black Soldier Fly larvae is superior to other commonly used protein sources, such as cricket, mealworm, fishmeal, chicken meal, corn and soy. Black Soldier Fly larvae is rich in protein and contains high levels of calcium and other essential nutrients. For example, Black Soldier Fly larvae may be reared on fermented organic waste for a 12-15 day growth period and harvested prior to reaching the pupae stage (about twice as fast as crickets). The harvested larvae may then be processed into one or more product protein lines, such as live larvae, dried larvae, a high-quality protein additive, and a nutrient-rich soil amendment. In particular, the processed Black Soldier Fly larvae may be used as a protein source in pet food, aquaculture feed and/or agricultural feed.

Various embodiments disclosed herein are directed at an apparatus and a method for breeding Black Soldier Flies. In particular, the apparatuses disclosed herein may be characterized as an enclosed reproductive habitat for Black Soldier Flies. Continuous loading of pupae and continuous removal of laid eggs may keep the enclosed reproductive habit at a generally stable Black Soldier Fly population (i.e., density). Accordingly, the embodiments of the apparatus and method disclosed herein may be used to improve the yield of Black Soldier Fly eggs from a continuous population of Black Soldier Flies. With all else being equal, by increasing egg production, greater quantities of Black Soldier Fly larvae may be reared, and ultimately harvested, for use as a source of protein. Thus, the use of the embodiments of the apparatus and method disclosed herein may lead to the production of Black Soldier Fly larvae in an economically viable and efficient manner.

As will be described below, another aspect of the teachings described herein is to induce Black Soldier Fly mating, to encourage female Black Soldier Flies to oviposit eggs (i.e., lay eggs), and to encourage pupae hatching and migration into a mating area. More particularly, in accordance with the teachings herein, the yield of Black Soldier Fly eggs from a continuous population of Black Soldier Flies may be improved through an interchange of lighting periods that induce or encourage different behaviour.

FIG. 1 illustrates an apparatus, referred to generally as 100, for breeding Black Soldier Flies. Apparatus 100 includes a fly enclosure 102, a first lighting device 104 and a second lighting device 106. Fly enclosure 102 defines an interior space 108 in which adult Black Soldier Flies are free to fly, mate, lay eggs, and otherwise move around as they please. First lighting device 104 (also referred to as lure lighting device 104) is operable to emit a first light 118 (also referred to as lure light 118) having a wavelength range that may attract Black Soldier Flies. Lure light 118 may have a wavelength range with a lower limit of about 280 nanometers and an upper limit of about 400 nanometers. More preferably, lure light 118 may have a wavelength range substantially between about 350 and 400 nanometers. As will be described in more detail below, lure lighting device 104 may be activated (i.e., turned on) to draw recently hatched Black Soldier Flies into interior space 108 so that they can begin mating.

Second lighting device 106 (also referred to as mating lighting device 106) is operable to emit a second light 120 (also referred to as mating light 120) having a wavelength range that may induce mating of Black Soldier Flies. A low level of broad-spectrum visible light with augmentation in the red and blue regions has been found proficient at inducing mating between Black Soldier Flies. Mating light 120 may have a wavelength range with a lower limit of about 380 nanometers and an upper limit of about 740 nanometers. More preferably, mating light 120 may have a wavelength range substantially between about 410 and about 730 nanometers. As will be described in more detail below, mating lighting device 106 may be activated (i.e., turned on) to illuminate interior space 108 of the fly enclosure 102 with mating light 120 to induce Black Soldier Flies in interior space 108 to mate.

In the example shown, fly enclosure 102 is rectangular, having opposed top and bottom sides $102_1$ and $102_2$, opposed front and rear sides $102_3$ and $102_4$, and opposed lateral sides $102_5$ and $102_6$. In alternative embodiments, fly enclosure 102 may have another suitable shape, e.g., cylindrical, square, etc. In large-scale commercial operations, multiple apparatuses 100 may be arranged in series (e.g., end-to-end). In these cases, it may be convenient for fly enclosure 102 to be rectangular so that space may be used more efficiently.

Fly enclosure 102 may be formed from a number of materials. Preferably, fly enclosure 102 is formed from a mesh material, e.g., fine pore window screen, plastic mesh, and/or No-See-Um netting. The mesh material of fly enclosure 102 in FIG. 1 has been omitted to allow for clear illustration of elements within fly enclosure 102. In the example shown, fly enclosure 102 is held open (i.e., maintains its shape) through attachment to a support frame 105. Support frame 105 may be made of metal, plastic, fiberglass, or any other suitable rigid or semi-rigid material. For example, fly enclosure 102 may be formed by attaching each corner of the mesh material to a corresponding corner of support frame 105. In other embodiments, fly enclosure 102 may be formed by wrapping the mesh material around support frame 105. Effectively, fly enclosure 102 may be formed from any material, or any combination of materials, that prevents Black Soldier Flies from escaping interior space 108 while permitting air exchange with the surrounding environment. In embodiments where a mesh material is used in fly enclosure 102, the pore size is preferably fine enough to prevent the entry of unwanted organisms (e.g., wasps, bees, hornets, etc.) into fly enclosure 102.

Gravid (i.e., pregnant) Black Soldier Flies are drawn to irregularities (corners, folds, nooks, crannies, tight spaces, etc.) as locations for laying eggs. As a result, such irregularities are preferably kept to a minimum within fly enclosure 102. For example, one or more sides $102_1$-$102_6$ of fly enclosure 102 may be smooth with rounded edges so that junctures between adjacent sides of fly enclosure 102 do not form sharp corners.

Fly enclosure 102 may range in size. In at least one embodiment, fly enclosure 102 may have an internal volume between about 0.5 and about 10 cubic meters ($m^3$). For example, preferably, fly enclosure 102 has an internal volume between about 1 and 2 $m^3$. More preferably, fly enclosure 102 has a volume of approximately 1.4 $m^3$. A number of factors may determine the size of fly enclosure 102, such as, for example, maintenance and cleaning considerations, light diffusion, and providing a density of Black Soldier Flies suited for mating. For example, the width of fly enclosure 102 may be limited to between about 0.5 to about 0.7 meters (m) to allow an operator to reach across for maintenance and/or cleaning purposes. Alternatively, or in addition, the height of fly enclosure 102 may be limited to approximately 3 m or less, or more preferably to between about 1.2 and about 1.8 m, based on light diffusion from above.

The density of Black Soldier Flies within fly enclosure 102 may be important from a mating perspective. Black Soldier Flies have a courtship ritual that requires close proximity. A male Black Soldier Fly may detect a suitable female Black Soldier Fly with which to mate by observing the female flying past a contrast, such as a black fly against a bright sky. As will be described in more below, such a contrast may be enhanced or better replicated by the inclusion of one or more contrast panels 128, e.g., at an upper portion of fly enclosure 102. Accordingly, if the density of Black Soldier Flies is too low, mating rates will be suboptimal (i.e., not enough male Black Soldier Flies will detect or identify mates).

On the other hand, if the density of Black Soldier Flies is too high, mating rates are also suboptimal. Since Black Soldier Flies begin their mating ritual in flight, an overly dense fly enclosure 102 can disrupt normal flying patterns. Simply stated, when the density is too high, the Black Soldier Flies are confounded and cannot identify a mate. The preferred Black Soldier Fly density in interior space 108 of fly enclosure 102 may range between about 7,000 and 40,000 flies per $m^3$. Accordingly, for a fly enclosure 102 with a volume of about 1.4 $m^3$, between about 10,000 and 50,000 adult Black Soldier Flies may occupy interior space 108 at a given time. It was found that by using a controlled density of adult Black Soldier Flies and using a lighting schedule with different types of lights having certain wavelengths and intensities as described herein can greatly increase egg production. For example, some test results have shown that there may be almost a 10-fold increase in egg production over the course of a day.

The lifespan of an adult Black Soldier Fly is about 6-15 days, and, for example, 7-10 days, depending on humidity (e.g., 50-90%), temperature (e.g., 22-35° C.) and/or stored energy, such as protein and fat levels. Deceased Black Soldier Flies may be removed from interior space 108 of fly enclosure 102 at a suitable interval. For example, deceased Black Soldier Flies may be removed from fly enclosure 102 every other day (i.e., about every 48 hours). Alternatively, they may be removed about every 24 hours. As described above, gravid Black Soldier Flies consider irregularities as potential sites for laying eggs. Deceased Black Soldier Flies, e.g., laying on bottom side $102_2$ of fly enclosure 102, may present such an irregularity. For this reason, when it comes to removing deceased Black Soldier Flies from fly enclosure 102, a shorter interval may be preferred over a longer interval. This may reduce the number of eggs that are laid on deceased Black Soldier Flies.

In at least one embodiment, fly enclosure 102 has at least one sealable opening to permit removal of the deceased Black Soldier Flies. For example, the sealable opening may be a zipper, valve, gate, port, or Velcro® flap. In the example shown, an access port 132 is provided at bottom side $102_2$ of fly enclosure 102 to permit periodic removal of the deceased Black Soldier Flies. In some cases, a suction head may be inserted into interior space 108 through the sealable opening (e.g., access port 132) to remove (i.e., vacuum up) the deceased Black Soldier Flies from the bottom side $102_2$ of fly enclosure 102. In the example shown, bottom side $102_2$ of fly enclosure 102 is funnel-shaped so that deceased Black Soldier Flies may collect in one general area under gravity to facilitate removal.

In some embodiments, a vacuum system (not shown) may also be included and used to remove deceased Black Soldier Flies from fly enclosure 102. As an example, the vacuum system may be turned on periodically to remove the deceased Black Soldier Flies that have collected on bottom side $102_2$ of fly enclosure 102. The vacuum system can transport the deceased Black Soldier Flies to a collection vessel. The deceased Black Soldier Flies which accumulate in the collection vessel can be used as a chitin product. In the example shown, such a vacuum system may be advantageously connected to access port 132 which is located at the lowest point of the funnel-shaped bottom side $102_2$. In this context, access port 132 may be referred to as a "vacuum port". It will be appreciated that a vacuum system may be connected to one or more fly enclosures 102. That is, a single vacuum system may be used to remove deceased Black Soldier Flies across multiple fly enclosures 102.

In at least one embodiment, apparatus 100 further includes an egg-laying region 110 that is locatable in interior space 108. As shown, it may be convenient to locate egg-laying region 110 in a lower portion of interior space 108 (i.e., above bottom side $102_2$), e.g., to facilitate egg removal, cleaning and/or maintenance. In the example shown, egg-laying region 110 is suspended above bottom side $102_2$ of fly enclosure 102 by cables 115 or another suitable mechanism. Cables 115 are connected to support frame 105. In one or more alternative embodiments, egg-laying region 110 may be located in other suitable locations in interior space 108. In at least one embodiment, apparatus 100 may include multiple egg-laying regions 110 located at different areas in interior space 108.

Egg-laying region 110 may include one or more egg blocks 111 on which gravid Black Soldier Flies may oviposit eggs and/or an attractant substance that may attract the gravid Black Soldier Flies to the one or more egg blocks 111. The attractant substance typically omits a pungent odour to indicate a potential food source. For example, one or more egg blocks may be placed on an attractant container that holds the attractant substance and/or one or more water bins. Each egg block 111 may include a structure (e.g., cardboard, plastic) having a series of folds and/or flutes oriented in many directions, and/or other irregularities to create an inviting oviposition site. In the example shown, each egg block 111 is a cardboard structure with three folds (giving egg blocks 111 an "M"-shape). Each egg block 111 may include a plurality of pores to further encourage ovipositing. The pores create even more irregularities in the surface of egg blocks 111. The pores are not shown due to their small size relative to the scale of FIGS. 1 and 2.

In at least one embodiment, fly enclosure 102 has at least one sealable opening to permit removal of Black Soldier Fly eggs, e.g., from egg-laying region 110, and/or to perform general maintenance or cleaning. In the example shown, front side $102_3$ of fly enclosure 102 includes a laterally extending slit 125. Slit 125 may be sealed and unsealed through lateral movement of a suitable mechanism such as a zipper. Other ways of sealing/unsealing slit 125 are possible, such as, for example, a hook and pile fastener. In one or more alternative embodiments, the sealable opening may be the same one used to remove deceased Black Soldier Flies (e.g., access port 132).

In the example shown, apparatus 100 further includes a pupae cartridge enclosure 112. Pupae cartridge enclosure 112 defines an interior cartridge space 114. As will be described in more detail below, interior cartridge space 114 of pupae cartridge enclosure 112 is in communication with interior space 108 of fly enclosure 102 through one or more lure ports 116.

In the example shown, pupae cartridge enclosure 112 is rectangular, having opposed top and bottom walls $112_1$ and $112_2$, opposed front and rear walls $112_3$ and $112_4$, and opposed lateral walls $112_5$ and $112_6$. In one or more alternative embodiments, pupae cartridge enclosure 112 may have another suitable shape, e.g., cylindrical, square, etc. As described above, in large-scale commercial operations, multiple apparatuses 100 may be arranged in series (e.g., end-to-end). Similar to fly enclosure 102, in these cases, it may be convenient for pupae cartridge enclosure 112 to be rectangular so that space may be used more efficiently.

Pupae cartridge enclosure 112 may be formed from a number of materials, e.g., plastic, corrugated plastic, glass, metal, or a combination thereof. Rates of pupae hatching within pupae cartridge enclosure 112 may substantially increase in the absence of light. Accordingly, to promote hatching of pupae in interior cartridge space 114, it may be advantageous for pupae cartridge enclosure 112 to be substantially impervious to light. For example, one or more of walls $112_1$-$112_6$ may substantially prevent stray light from passing therethrough. For example, a "black-out" material may be applied to one or more of sides $112_1$-$112_6$ of pupae cartridge enclosure 112 to prevent passage of light. In alternative embodiments, fly enclosure 102 and pupae cartridge enclosure 112 may be made from the same material, e.g., mesh material. In such embodiments, the screening material surrounding pupae cartridge enclosure 112 may be covered (e.g., blanketed or draped) with a "black-out" material to substantially block light diffusion into interior cartridge space 114. A pupae cartridge enclosure 112 made with solid material (e.g., corrugated plastic) may be more durable and impervious to light compared to a pupae cartridge enclosure 112 made with mesh material.

In the example shown, lateral wall $112_6$ of pupae cartridge enclosure 112 faces lateral side $102_5$ of fly enclosure 102.

Accordingly, lateral wall $112_6$ may be characterized as dividing wall $112_6$ that separates interior cartridge space 114 of pupae cartridge enclosure 112 from interior space 108 of fly enclosure 102. In at least one embodiment, lateral wall $112_6$ defines lateral side $102_5$ of fly enclosure 102. In such embodiments, the mesh material of fly enclosure 102 may be sealed around the perimeter of dividing wall $112_6$. Alternatively, dividing wall $112_6$ may face (e.g., overlay) the mesh material of fly enclosure 102 at lateral side $102_5$. In the example shown, lure ports 116 are formed in dividing wall $112_6$.

As described above, interior cartridge space 114 of pupae cartridge enclosure 112 is in communication with interior space 108 of fly enclosure 102 through one or more lure ports 116. The number and/or size or lure ports 116 may vary as desired. For example, only one lure port 116 may be provided. Alternatively, more than one lure port 116 such as, but not limited to, six lure ports 116, for example, may be provided. In the example shown, three lure ports $116_1$, $116_2$ and $116_3$ are provided in dividing wall $112_6$. In at least one embodiment, lure ports 116 may be selectively opened and closed. Lure ports 116 may be closed to prevent stray light from passing into interior cartridge space 114 of pupae cartridge enclosure 112. Lure ports 116 may be opened to coincide with when the lure lighting device 104 is activated (i.e., turned on) and closed when lure lighting device 104 is not activated (i.e., turned off).

In the example shown, lure ports $116_1$, $116_2$ and $116_3$ are circular. In alternative embodiments, lure ports 116 may have another shape, e.g., elliptical. As described above, gravid Black Soldier Flies are attracted to irregular surfaces (e.g., corners, folds, narrow spaces) for laying their eggs. For this reason, lure port 116 having corners (e.g., square, rectangular, triangular, etc.), while possible, may generally be avoided. For example, a square lure port 116 would create additional folds and crevices for possible egg laying. By keeping seams and corners to a minimum, apparatus 100 encourages gravid Black Soldier Flies to lay their eggs in the egg-laying region 110 (e.g., on egg blocks 111).

Apparatus 100 may further include one or more replaceable pupae cartridges 134 into which Black Soldier Fly pupae are loaded. For example, each pupae cartridge 134 may hold between 2,000 and 10,000 pupae depending on loading rate. In the example shown, pupae cartridges 134 are loaded onto a rack 135 in interior cartridge space 114 of pupae cartridge enclosure 112. Alternatively, pupae cartridges 134 may be stacked, e.g., one on top of the other, in interior cartridge space 114. Alternatively, or in addition, one or more pupae cartridges 134 may be placed on bottom wall $112_4$ of pupae cartridge enclosure 112.

In at least one embodiment, pupae cartridges 134 may have an outer housing that is partially, or entirely, formed of a transparent (i.e., see-through) material. This may allow for visual inspection of the Black Soldier Fly pupae therein, e.g., to estimate a time until hatching begins and/or to verify the health of the pupae before loading into interior cartridge space 114 of pupae cartridge enclosure 112.

In at least one embodiment, pupae cartridges 134 may have an outer housing that is formed entirely by a material that is impervious to light (e.g., an opaque plastic or metal). Accordingly, little to no light may pass into such pupae cartridges 134. In these embodiments, pupae cartridge enclosure 112 may be omitted from apparatus 100 or may be made from material that does not block light. That is, pupae cartridge enclosure 112 may not be required to block light from reaching pupae cartridges 134.

Pupae cartridge enclosure 112 may include a door (not shown) to permit exchange of pupae cartridges 134 in and out of interior cartridge space 114. As an example, the door may be a flap cut into lateral side $112_5$ of pupae cartridge enclosure 112. As another example, front wall $112_3$ may be slidably connected along the edges of top and bottom walls $112_1$ and $112_2$. In this example, front wall $112_3$ can be slid laterally to gain access to interior cartridge space 114. As yet another example, top wall $112_1$ may be connected to an adjacent wall of pupae cartridge enclosure 112, e.g., rear wall $112_4$, by one or more hinges. In this example, top wall $112_1$ of pupae cartridge enclosure 112 may be characterized as the door. A fresh pupae cartridge 134 may be exchanged with one in which all pupae have likely hatched. For example, an exchange may be made every 48 hours, or at another suitable interval.

To encourage hatching, pupae cartridges 134 are kept in the dark within pupae cartridge enclosure 112. The pupae stage generally lasts 9-20 days, and for example, 7-10 days depending on factors such as, for example, movement, proximity to other moving pupae, level of light, temperature and humidity. Following the pupae stage, an adult fly will emerge. Accordingly, it may improve loading if pupae cartridges 134 are loaded into pupae cartridge enclosure 112 when they are close to hatching (e.g., after day 5 or 6).

In at least one embodiment, when the pupae hatch they are allowed to escape from their pupae cartridge 134 and move (i.e. crawl) into interior cartridge space 114 of pupae cartridge enclosure 112. In such an embodiment, pupae cartridge enclosure 112 provides a containment function. That is, walls $112_1$-$112_6$ contain the hatched Black Solider Flies within cartridge enclosure 112. Black Soldier Flies are negatively phototactic (i.e., drawn to light) so light may be used to stimulate migration in desired directions. Accordingly, the hatched Black Soldier Flies may be drawn through lure ports 116 and into interior space 108 of fly enclosure 102 by turning on lure lighting device 104. As described above, one or more of walls $112_1$-$112_6$ of pupae cartridge enclosure 112 may be "blacked-out". This may prevent stray light from reaching pupae cartridges 134. Other advantages to keeping the pupae cartridges 134 in the dark within pupae cartridge enclosure 112 may include discouraging mating in interior cartridge space 114 and/or to emphasize light contrast when luring the recently hatched Black Soldier Flies from their respective pupae cartridges 134 into interior space 108 of fly enclosure 102.

In the example shown, three pupae cartridges $134_1$, $134_2$ and $134_3$ are coupled to corresponding lure ports $116_1$, $116_2$ and $116_3$. In the example shown, each lure port 116 includes a frustoconical conduit 145 connected thereto. Frustoconical conduits 145 may be connected to a corresponding lure port 116 in any suitable fashion (e.g., snap fit, adhesive, mechanical fasteners, etc.). Frustoconical conduit 145 allows recently hatched Black Soldier Flies to pass of from their respective pupae cartridge 134 into interior space 108 of fly enclosure 102. At the same time, frustoconical conduit 145 may impede passage of Black Soldier Flies from the interior space 108 back into the pupae cartridge 134, through lure port(s) 116.

Not only may frustoconical conduit 145 prevent recently hatched Black Soldier Flies from returning to the pupae cartridge 134 from which they emerged, but it may also reduce the likelihood of adult Black Soldier Flies that are already in interior space 108 (specifically gravid Black Soldier Flies) from passing into the pupae cartridges 134 and laying eggs therein. The shape of frustoconical conduit 145 together with the lack of light in pupae cartridge enclosure 112 can keep Black Soldier Flies from flying back through frustoconical conduit 145 once in interior space 108 (i.e., in reverse). In this context, frustoconical conduit 145 may be characterized as a "one-way" conduit. In some embodiments, frustoconical conduit 145 may be a truncated plastic cone that includes a plurality of perforations. These perforations may allow a greater proportion of lure light 118 to reach lure port(s) 116 compared to a non-perforated (i.e., solid) frustoconical conduit. Preferably, these perforations are sized so that a Black Soldier Fly may not pass through.

Pupae cartridge enclosure 112 can still provide a containment function even in embodiments where pupae cartridges 134 are coupled to lure ports 116. In the event a pupae cartridge 134 is not fully sealed (e.g., partially open lid), hatched Black Soldier Flies that escape through the partially open lid are contained within pupae cartridge enclosure 112. In other words, they are not released to the surrounding environment.

The size of pupae cartridge enclosure 112 may be determined by the size and/or number of pupae cartridges (e.g., pupae cartridges 134) loaded therein. In at least one embodiment, each pupae cartridge may be about 25 centimeters (cm) by about 30 cm by about 21 cm. Alternatively, each pupae cartridge 134 may be about 50 cm by about 30 cm by about 21 cm. In at least one embodiment, the pupae cartridges 134 may have differing sizes with respect to one another.

In at least one embodiment, apparatus 100 may include two or more pupae cartridge enclosures 112. The inclusion of additional pupae cartridge enclosures 112 may increase loading rate, e.g., the number of recently hatched Black Soldier Flies that enter fly enclosure 102 through the one of more lure ports 116. For example, an additional pupae cartridge enclosure (similar to pupae cartridge enclosure 112) may be located adjacent lateral end $102_6$ of fly enclosure 102.

In the example shown, lure lighting device 104 is i) spaced apart from lure ports $116_1$, $116_2$, and $116_3$, and ii) oriented to generally face lure ports $116_1$, $116_2$ and $116_3$. In this arrangement, lure light 118 that is emitted from lure lighting device 104 may be visible, through lure ports 116, to recently hatched Black Soldier Flies within pupae cartridge enclosure 112. More particularly, this arrangement may facilitate a high proportion of emitted lure light 118 to travel in a direction toward lure ports 116. Such an arrangement may provide a strong luring effect since sufficient lure light 118 is visible from pupae cartridge enclosure 112 through lure ports 116. Lure lighting device(s) 104 may be spaced about 0.5 to 5 meters (m) apart from lure port(s) 116. More preferably, lure lighting device(s) 104 may be spaced about 0.5 to 2.5 m apart from lure port(s) 116.

In the example shown, in which each pupae cartridge 134 is connected to a corresponding lure port 116, recently hatched Black Soldier Flies may be afforded a direct line of sight to lure lighting device 104 and, as a result, to lure light 118 emitted by lure lighting device 104. It will be appreciated that additional lure lighting devices 104 may be included to better direct lure light 118 toward lure ports 116.

Dividing wall $112_6$ is preferably substantially impervious to light, e.g., as described above. This can allow dividing wall $112_6$ to impede light intended for interior space 108 of fly enclosure 102 from diffusing into interior cartridge space 114 of pupae cartridge enclosure 112. If stray light diffuses through dividing wall $112_6$, newly hatched Black Soldier Flies may bump up against the walls of pupae cartridges 134 trying to reach that light source. Accordingly, it is preferable for lure light 118 to enter pupae cartridge 134, through lure ports 116, along one defined path to make it easier for hatched Black Solider Flies to exit that pupae cartridge 134 (and enter fly enclosure 102).

In the example shown, lure lighting device 104 is located outside fly enclosure 102. Lure lighting device 104 can be mounted in any suitable fashion. Lure lighting device 104 is shown suspended adjacent to lateral side $102_6$ of fly enclosure 102 by a cable 155 that extends downward from the ceiling. Alternatively, or in addition, lure lighting device 104 may be supported above the floor, e.g., by one or more legs. Alternatively, or in addition, lure lighting device 104 may be mounted to support frame 105. Since lure lighting device 104 is located outside fly enclosure 102, unintended surfaces on which gravid Black Soldier Flies may oviposit egg are limited. This may simplify maintenance (e.g., changing bulbs) and/or cleaning of fly enclosure 102. It will be appreciated that a distance between lure lighting device 104 and lure ports 116 (or dividing wall $112_6$) may vary according to the length of fly enclosure 102 (lateral side $102_5$ to lateral side $102_6$).

Figure 2:
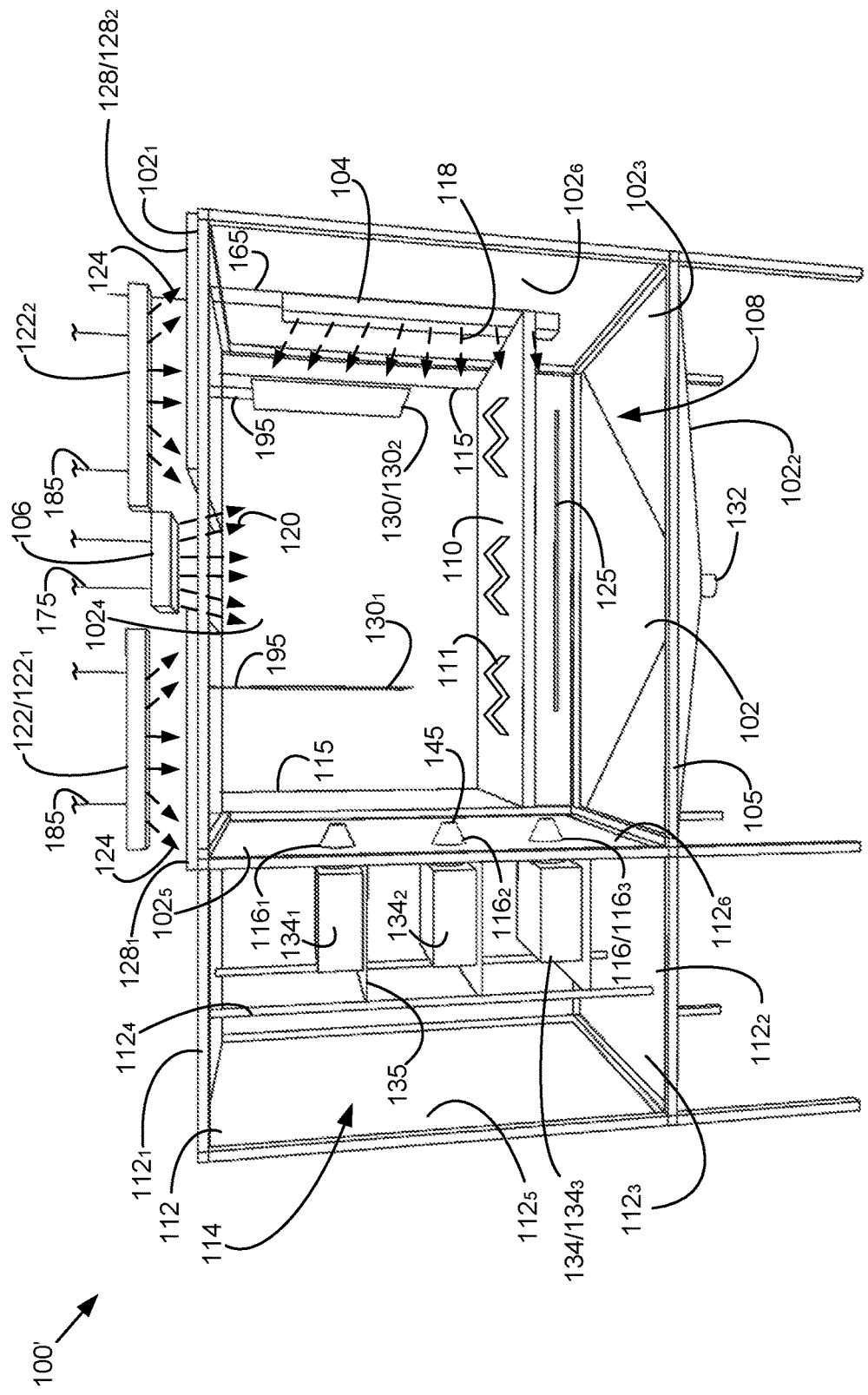
FIG. 2 is a front view of an apparatus for breeding Black Soldier Flies, in accordance with a second example embodiment.

Referring to FIG. 2, in an alternative embodiment, apparatus 100' includes a lure lighting device 104 that is located within fly enclosure 102. Lure lighting device 104 of FIG. 2 can be mounted in any suitable fashion. Lure lighting device 104 is shown suspended from support frame 105 by cables 165. Alternatively, lure lighting device 104 of FIG. 2 may be suspended within fly enclosure 102, e.g., by a cable that extends downward from the ceiling. Alternatively, or in addition, lure lighting device 104 of FIG. 2 may be supported above the floor, e.g., by one or more legs. As shown by comparison of FIG. 2 to FIG. 1, when luring lighting device 104 is located in interior space 108 of fly enclosure 102, it is closer to lure ports 116. This may allow lure light 118 that is emitted by luring lighting device 104 to have greater visibility in interior cartridge space 114 of pupae cartridge enclosure 112, thereby having a greater luring effect. Locating lighting device 104 within fly enclosure 102 may also reduce the overall size of apparatus 100'. This space savings may be particularly significant when multiple apparatuses 100' are arranged in series (i.e., side-by-side or end-to-end).

Referring to FIGS. 1 and 2, by locating lure lighting device 104 so that it is both (i) spaced apart from lure ports 116 and (ii) oriented to generally face lure ports 116, lure light 118 emitted by lure lighting device 104 may be visible, through lure ports 116, to the recently hatched Black Soldier Flies within pupae cartridge enclosure 112. As a result, recently hatched Black Soldier Flies may be drawn all the way into interior space 108 of fly enclosure 102 by lure light 118. This may not be the case if lure lighting device 104 was located at lure ports 116, in pupae cartridges 134, and/or within frustoconical conduits 145. In these cases, recently hatched Black Soldier Flies may stop prior to entering interior space 108, thereby not entering the mating area.

As described above, lure light 118 may have a wavelength range with a lower limit of about 280 nanometers and an upper limit of about 400 nanometers. For example, more preferably, lure light 118 may have a wavelength range substantially between about 350 and 400 nanometers. Light within such a wavelength range has been shown to effectively attract Black Soldier Flies even at low intensities (e.g., less than 10 lux).

Lure lighting device 104 may include one or more bulbs, tubes, lamps, or a combination thereof. For example, lure lighting device 104 may include one or more Actinic BL TL(-K)/TL-D(-K) lighting tubes made by Philips®. This lighting tube emits long-wave UV-A radiation in the 350-

400 nanometer range and has a UV-B/UV-A ratio less than 0.1% (UV-B 280-315 nanometers). Alternatively, one or more other lighting bulbs, tubes, or lamps may be selected that emit light having a wavelength proficient at attracting insects (particularly Black Soldier Flies). For embodiments in which lure lighting device 104 includes a lighting tube (also referred to as a tube light), the tube light is preferably oriented so that it is substantially parallel to dividing wall $112_6$. Such an arrangement may direct a high proportion of lure light 118 toward lure ports 116, which may increase its luring effect.

Referring again to FIG. 1, mating lighting device 106 is located above fly enclosure 102 and oriented to direct mating light 120 into interior space 108 of fly enclosure 102. In this way, at least some of the Black Soldier Flies in interior space 108 are exposed to mating light 120. Mating lighting device 106 can be mounted in any suitable fashion. For example, mating lighting device 106 may be mounted to support frame 105. In the example shown, mating lighting device 106 is suspended above top side $102_1$ of fly enclosure 102 by cables 175 that extend downward from the ceiling. Alternatively, or in addition, one or more mating lighting devices 106 may be located adjacent (e.g., in front of) front side $102_3$ and/or adjacent (e.g., behind) rear side $102_4$ of fly enclosure 102 and oriented to direct mating light 120 into interior space 108 of fly enclosure 102.

As described above, mating light 120 may have a wavelength range with a lower limit of about 380 nanometers and an upper limit of about 740 nanometers. For example, more preferably, mating light 120 may have a wavelength range substantially between about 410 and 730 nanometers. Light with such a wavelength range may induce Black Soldier Flies to mate. As described above, a low level of broadspectrum visible light with augmentation in the red and blue regions has been found proficient at inducing mating between Black Soldier Flies.

Mating lighting device 106 may include one or more bulbs, tubes, lamps, or a combination thereof. For example, mating lighting device 106 may include a King Plus 1200 W lamp. This lamp includes multiple individual LEDs that each emit light at specific wavelengths or within a specific wavelength range. For example, the King Plus 1200 w lamp emits the following wavelengths and wavelength ranges of light: 410 nm, 430-440 nm, 450-475 nm, 620-630 nm, 650-670 nm and 730 nm. In at least one embodiment, the King Plus 1200 W lamp may be modified by removing the individual LEDs responsible for emitting UV light (i.e., 410 nm and below). Alternatively, one or more other lighting bulbs, tubes, or lamps may be selected that emit light having a wavelength proficient at inducing Black Soldier Flies to mate.

The intensity of mating light 120, together with its wavelength, may be important in the inducement of Black Soldier Fly mating. That is, one without the other may not be sufficient to stimulate mating. Mating light 120 may start to induce mating behaviour at or above an intensity of about 1500 lux. However, all else being equal, the higher the intensity of mating light 120, the greater its effect to induce mating. For example, mating light 120 at or above about 30,000 lux has shown a proficiency to induce mating. Accordingly, it may be preferable to have mating light 120 of the highest possible intensity diffuse into as much of interior space 108 as possible.

To enhance mating rates, one or more mating lighting devices 106 may be selectively positioned around fly enclosure 102 so that mating light 120 of sufficient intensity diffuses into as much of interior space 108 as possible. Light intensity drops with the square of the distance from the light source so it may be preferable to position mating lighting devices 106 close to fly enclosure 102. In the example shown, mating lighting device 106 is located immediately above top side $102_1$ of fly enclosure 102 to make the most efficient use of the intensity of emitted mating light 120.

It will be appreciated that additional mating lighting devices 106 may be included in apparatus 100 and arranged to better illuminate regions of interior space 108 with mating light 120 of sufficient intensity. For example, the determination of how many mating lighting devices 106 to include in apparatus 100 may be based on the size of fly enclosure 102, the relative separation between mating lighting devices 106 and fly enclosure 102, and/or the strength of the one or more tubes, bulbs, or lamps used in mating lighting devices 106. For example, in an alternative embodiment, two spaced apart mating lighting devices 106 may be included to direct mating light 120 into interior space 108.

Mating lighting device 106 may be adjusted in the vertical plane (i.e., up and down) to modify the intensity of mating light 120 that reaches interior space 108 (i.e., the mating area). In at least one embodiment, mating lighting device 106 may be adjusted in the vertical plane by varying a length that cables 175 extend from the ceiling. A pulley may be included to simplify such adjustments. Alternatively, or in addition, mating lighting device 106 may have a control dial that allows for the intensity of the emitted mating light 120 to be adjusted (i.e., turned up or down) as desired.

Referring still to FIG. 1, as with lure lighting device 104, mating lighting device 106 is located outside fly enclosure 102 to limit unintended surfaces on which gravid Black Soldier Flies may oviposit eggs. As described above, this may simplify maintenance (e.g., changing bulbs) and/or cleaning of fly enclosure 102. Alternatively, in one or more other embodiments (not shown), one or more mating lighting devices 106 may be located within fly enclosure 102. When the mating lighting devices are located within fly enclosure 102, zones of greater light intensity may be created relative to when mating lighting devices 106 are located outside fly enclosure 102 (e.g., as shown in FIG. 1). This may increase mating rates. Furthermore, locating the one or more mating lighting devices 106 within fly enclosure 102 may reduce the overall size of the apparatus.

Under appropriate conditions, gravid Black Soldier Flies will oviposit eggs approximately 24-72 hours after mating. While mating light 120 may induce Black Soldier Flies to mate, they may also discourage gravid Black Soldier Flies from laying eggs. Gravid Black Soldier Flies may not lay eggs when mating lighting device 106 is activated (i.e., emitting mating light 120). Furthermore, when Black Soldier Flies are subjected to mating light 120 for extended durations, mating light 120 may gradually lose its effectiveness at inducing mating. Accordingly, it may be beneficial to provide gaps before and after the periods in which mating light 120 is emitted so that gravid Black Soldier Flies may oviposit eggs in such gaps. This may also have the added advantage of subjecting the Black Soldier Flies with contrasting light intensities. For example, the transition between light of different intensity may induce a change in Black Soldier Fly behaviour.

However, when mating lighting device 106 is off (i.e., mating light 120 not being emitted), interior space 108 of fly enclosure 102 may be quite dark. Black Soldier Flies tend to lower their activity in dark environments. While this may be useful in interior cartridge space 114 of pupae cartridge enclosure 112 to promote pupae hatching, keeping a base level of activity of the Black Soldier Flies in interior space 108 of fly enclosure 102 may be beneficial. For example, if interior space 108 of fly enclosure 102 is too dark, then gravid Black Soldier Flies may become inactive and, as a consequence, may not move toward egg-laying region 110 to lay eggs. These gravid Black Soldier Flies can be said to be below a base ovipositing activity level.

Referring to FIG. 1, apparatus 100 may further include a third lighting device 122 (also referred to as base lighting device 122). Base lighting device 122 is operable to emit a third light 124 (also referred to as base light 124). As discussed below, the emission of base light 124 into interior space 108 may ensure that gravid Black Soldier Flies maintain at least an activity level needed to oviposit eggs. That is, the emission of base light 124 may ensure that gravid Black Soldier Flies stay at or above a base ovipositing activity level. The emission of base light 124 may also help gravid Black Soldier Flies to locate ovipositing sites (e.g., egg blocks 111 in egg-laying region 110) and/or make it easier for operators to navigate their way around apparatus 100 (e.g., to perform maintenance or inspections). Preferably, base light 124 is emitted during periods in which mating light 120 is not emitted (i.e., the gaps described above). This may conserve energy. However, in other cases, base light 124 may be emitted at times mating light 120 is also being emitted.

Base lighting device 122 may include one or more bulbs, tubes, lamps, or a combination thereof. For example, base lighting device 122 may include one or more General Electric™ LED12ET8/G/4/840 tubes. Alternatively, a number of other bulbs, tubes and lamps may be selected.

Base lighting device 122 may be positioned and oriented so that, when activated (i.e., turned on), base light 124 illuminates interior space 108 of fly enclosure 102 to an illuminance above an ovipositing illuminance threshold. A Black Soldier Fly subjected to an illuminance above the ovipositing illuminance threshold may maintain at least the minimum activity level needed to oviposit (i.e., lay eggs). Conversely, a Black Soldier Fly subjected to an illuminance below the ovipositing illuminance threshold may not lay eggs. Instead, these "inactive" Black Soldier Flies may rest or conserve energy (i.e., not lay eggs). The ovipositing illuminance threshold may be about 1 lux. Alternatively, the ovipositing illuminance threshold may be about 2-6 lux, or higher.

In the example shown, apparatus 100 includes two spaced apart base lighting devices $122_1$ and $122_2$. Base lighting devices $122_1$ and $122_2$ are positioned and oriented so that, when activated (i.e., turned on), base light 124 illuminates interior space 108 of fly enclosure 102 to an illuminance above the ovipositing illuminance threshold. As shown, base lighting devices $122_1$ and $122_2$ are positioned at opposite ends of the mating lighting device 106 so that a minimal amount of base light 124 is blocked by mating lighting device 106.

It may be preferable to illuminate interior space 108 above the ovipositing illuminance threshold with base light 124. Providing a margin or buffer may reduce (or even eliminate) the number of Black Soldier Flies that become inactive when base light 124 is being emitted. In other words, a margin or buffer may reduce the number of Black Soldier Flies that do not have the minimum activity level to lay eggs. For example, if the ovipositing illuminance threshold is 5 lux, it may be preferable to illuminate interior space 108 to an illuminance about 25 lux with base light 124. If Black Soldier Flies are observed to be inactive when base light 124 is emitted, the illuminance of interior space 108 can be increased. For example, the illuminance of interior space 108 may be increased by increasing the intensity of base light 124, repositioning the one or more base lighting devices 122 to be closer to the fly enclosure, and/or including additional base lighting devices 122. However, if the illuminance of interior space 108 is too high (e.g., above 1500 lux), mating behaviour may be induced by base light 124. Accordingly, base light 124 preferably illuminates interior space 108 to an illuminance anywhere above the ovipositing illuminance threshold (e.g., about 1-6 lux) and below a mating inducing illuminance threshold (e.g., about 1500 lux).

Base lighting devices 122 can be mounted in any suitable fashion. For example, base lighting devices 122 may be mounted to support frame 105. In the example shown, base lighting devices $122_1$ and $122_2$ are suspended above top side $102_1$ of fly enclosure 102 by cables 185 that extend downward from the ceiling. Base lighting devices $122_1$ and $122_2$ are preferably positioned about 20 to 100 cm above or below mating lighting device 106. In the example shown, base lighting devices $122_1$ and $122_2$ are positioned (e.g., suspended) about 30 cm above mating lighting device 106. In this arrangement, sufficient base light 124 is able to pass around mating lighting device 106 to illuminate interior space 108 of fly enclosure 102 to an illuminance above the illuminance threshold. The vertical or horizontal spacing between base lighting devices 122 and mating lighting device 106 may be increased or decreased as desired while taking into account the designed light intensities that the flies should be exposed to within the interior space 108 to induce them to behave in a certain way. Alternatively, or in addition, one or more base lighting devices 122 may be located adjacent (e.g., in front of) front side $102_3$ and/or adjacent (e.g., behind) rear side $102_4$ of fly enclosure 102 and oriented to direct base light 124 into interior space 108 of fly enclosure 102.

It will be appreciated that more or less base lighting devices 122 may be used to illuminate interior space 108 to an illuminance above the illuminance threshold. For example, the determination of how many base lighting devices 122 to include in apparatus 100 may be based on the size of fly enclosure 102, the relative separation between base lighting devices 122 and fly enclosure 102, and/or the strength of the one or more tubes, bulbs, or lamps used in base lighting devices 122. For example, in an alternative embodiment, a single base lighting device 122 may be included. In another alternative embodiment, five base lighting devices 122 may be included.

In at least one embodiment, multiple apparatuses 100 may be arranged in series (e.g., side-by-side or end-to-end). In these embodiments, a base lighting device 122 may be positioned between two or more apparatuses 100. This base lighting device 122 may direct base light 124 into multiple (two or more) fly enclosures 102. It is contemplated that one base lighting device 122 may emit sufficient base light 124 to illuminate interior space 108 of two or more adjacent fly enclosures 102 to an illuminance above the illuminance threshold.

Similar to mating lighting device 106, base lighting device $122_1$ and/or base lighting device $122_2$ may be adjusted in the vertical plane (i.e., up and down) to modify the intensity of base light 124 that diffuses into interior space 108. In at least one embodiment, each base lighting device $122_1$ and $122_2$ may be adjusted in the vertical plane by varying a length that cables 185 extend from the ceiling. A pulley may be included to simplify such adjustments. Alternatively, or in addition, each base lighting device 122 may have a control dial that allows for the intensity of the emitted base light 124 to be adjusted (i.e., turned up or down) as desired.

Referring still to FIG. 1, as with lure lighting device 104 and mating lighting device 106, base lighting devices 122$_1$ and 122$_2$ are located outside fly enclosure 102 to limit unintended surfaces on which gravid Black Soldier Flies may oviposit eggs. As described above, this may simplify maintenance (e.g., changing bulbs) and/or cleaning of fly enclosure 102. Alternatively, in one or more other embodiments (not shown), one or more base lighting devices 122 may be located in interior space 108 of fly enclosure 102. When the one or more base lighting devices 122 are located within fly enclosure 102, the overall size of the apparatus may be reduced.

In one or more alternative embodiments, apparatus 100 may not include base lighting devices 122$_1$ and 122$_2$. In such embodiments, base light may be provided by sunlight. Sunlight on its own may provide sufficient base light to illuminate interior space 108 to an illuminance above the illuminance threshold. For example, apparatus 100 may be located proximate a window so that sunlight may pass through the window and into interior space 108 of fly enclosure 102. In one or more other alternative embodiments, the base light that enters the interior space 108 may be a combination of base light 124 (emitted from base lighting device 122) and sunlight.

Apparatus 100 may optionally include one or more contrast panels 128 to help male Black Soldier Flies identify female Black Soldier Flies with which to mate. Contrast panels 128 are preferably located so that male Black Soldier Flies can more easily see and engage with female Black Soldier Flies that are flying overhead. Contrast panels 128 are preferably light in color and translucent to mimic a bright sky. For example, in at least one embodiment, contrast panel 128 may be a high-density polyethylene (HDPE) sheet. Contrast panels 128 may be mounted to fly enclosure 102 and/or support frame 105 in any suitable fashion.

In the example shown, top side 102$_1$ of fly enclosure 102 includes two spaced apart contrast panels 128$_1$ and 128$_2$ that are coplanar and are generally aligned below corresponding base lighting devices 122$_1$ and 122$_2$. As shown, mating lighting device 106 is positioned between contrast panels 128$_1$ and 128$_2$. In this position, contrast panels 128$_1$ and 128$_2$ may not impede the path of mating light 120 emitted from mating lighting device 106. As a result, the full intensity of mating light 120 may enter interior space 108. Female Black Soldier Flies may fly between male Black Soldier Flies below and contrasting panel 128$_1$ and 128$_2$ above while being exposed to mating light 120. Such an arrangement may increase mating rates.

Contrast panels 128$_1$ and 128$_2$ may be mounted to support frame 105 so that they are positioned above top side 102$_1$ of fly enclosure 102. Alternatively, or in addition, contrast panels 128$_1$ and 128$_2$ may be secured to top side 102$_1$ of fly enclosure 102, e.g., by adhesive, stitching, clamps, or a combination thereof. In one or more alternative embodiments, contrast panels 128 may be integral with fly enclosure 102. In such embodiments, the mesh material of fly enclosure 102 may transition into contrast panels 128 (e.g., high-density polyethylene (HDPE) sheets) at specific locations.

Fly enclosure 102 may optionally include one or more resting surfaces 130 located in interior space 108. Resting surfaces 130 may provide additional surfaces for male Black Soldier Flies to rest and observe female Black Soldier Flies in flight. Preferably, resting surfaces 130 are formed of a mesh fabric or screen material so that they block minimal amounts of light. In the example shown, fly enclosure 102 includes two additional resting surfaces 130$_1$ and 130$_2$. Resting surfaces 130 may be suspended from top side 102$_1$ of fly enclosure 102 and/or contrast panels 128 in any suitable way, e.g., by adhesive, stitching, clamps, or a combination thereof. In the example shown, resting surfaces 130$_1$ and 130$_2$ are suspended by wires 195 from corresponding contrast panels 128$_1$ and 128$_2$ at the top side 102$_1$ of fly enclosure 102. In at least one embodiment, resting surfaces 130 are 35 cm by 20 cm in size. It will be appreciated that other sizes are possible. In one or more alternative embodiments, resting surfaces 130 may be located elsewhere in interior space 108, e.g., extending inward from front side 102$_3$ and/or rear side 102$_4$ of fly enclosure 102.

Apparatus 100 can include a controller 126 (FIG. 3) that is coupled to each of the lure, mating, and base lighting devices 104, 106 and 122. Controller 126 may be used to control operation (e.g., turn on and off) of the lure, mating, and base lighting devices 104, 106 and 122. In one or more alternative embodiments (not shown), apparatus 100 may not include controller 126. In such embodiments, each of the lure, mating and base lighting devices 104, 106 and 122 may be selectively operated (i.e., turned on and off manually), e.g., with a switch and/or button that is operationally coupled to the lighting devices 104, 106 and 122.

As will be described in more detail below, controller 126 may be wirelessly coupled to at least one of the lure, mating and base lighting devices 104, 106 and 122, e.g., by Bluetooth®. Alternatively, controller 126 may be directly or indirectly coupled to each of the lure, mating and base lighting devices 104, 106 and 122 by a suitable type of electrical wiring. Alternatively, a combination of wired and wireless connections may be used.

Figure 3:
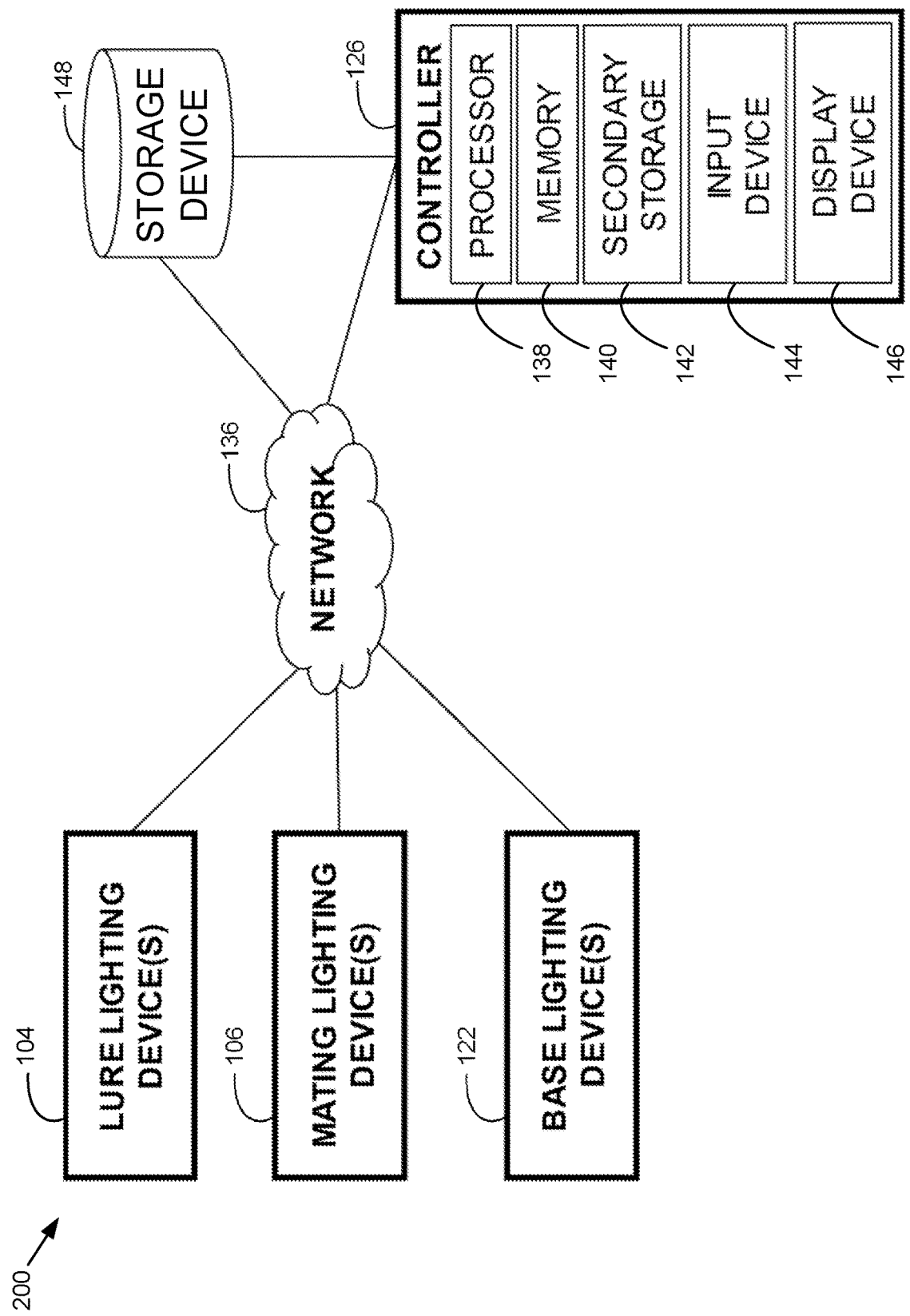
FIG. 3 is a block diagram displaying an example embodiment of a system for controlling lighting devices of the apparatus shown in FIG. 1 or FIG. 2 over a network.

Referring to FIG. 3, illustrated therein is a block diagram of an example embodiment of a system 200 for controlling the lighting devices of apparatus 100 (FIG. 1) or apparatus 100' (FIG. 2). System 200 includes controller 126 coupled to each of the lure, mating and base lighting devices 104, 106 and 122 across a network 136. Controller 126 may be located remotely from and accessible to the lure, mating and base lighting devices 104, 106 and 122 across network 136. It will be appreciated that in one or more alternative embodiments, system 200 may include more or less lighting devices.

Alternatively, or in addition, controller 126 may be locally connected with any one of the lure, mating, and base lighting devices 104, 106 and 122. As described above, suitable electrical wiring may be used to connect any one of the lure, mating and base lighting devices 104, 106 and 122 with controller 126.

Referring still to FIG. 3, controller 126 may interact with lure, mating and base lighting devices 104, 106 and 122 across communication network 136. For example, controller 126 may send a signal to any one of the lure, mating and base lighting devices 104, 106 and 122, across network 136, to turn that lighting device on or off.

Controller 126 may include at least one processor 138 and a memory 140, and may be an electronic tablet device, a personal computer, a workstation, a server, a portable computer, a mobile device, a personal digital assistant, a laptop, a smart phone, a wireless application phone (WAP), an interactive television, a video display terminal, a single board computer (SBC), a portable electronic device, or any combination of these. Secondary storage 142 may also be provided within controller 126. Generally, secondary storage 142 may be any suitable storage device such as a hard disk drive, a solid state drive, a memory card, or a disk (e.g. CD, DVD, or Blu-ray etc.).

In at least one embodiment, processor 138 of controller 126 may be configured to operate logging software that is stored in memory 140 and/or secondary storage 142. In such embodiments, a lighting schedule for automating operation of the lighting devices may be entered into the logging software and stored in memory 140 and/or secondary storage 142 of controller 126. In this way, when the program instructions of the logging software are executed by the processor 138, the processor 138 is configured to cause the controller 126 to automate the operation of lure, mating and base lighting devices 104, 106 and 122. That is, controller 126 may automatically turn the lure, mating, and base lighting devices 104, 106 and 122 on and off at specific times according to the stored lighting schedule.

Figure 4:
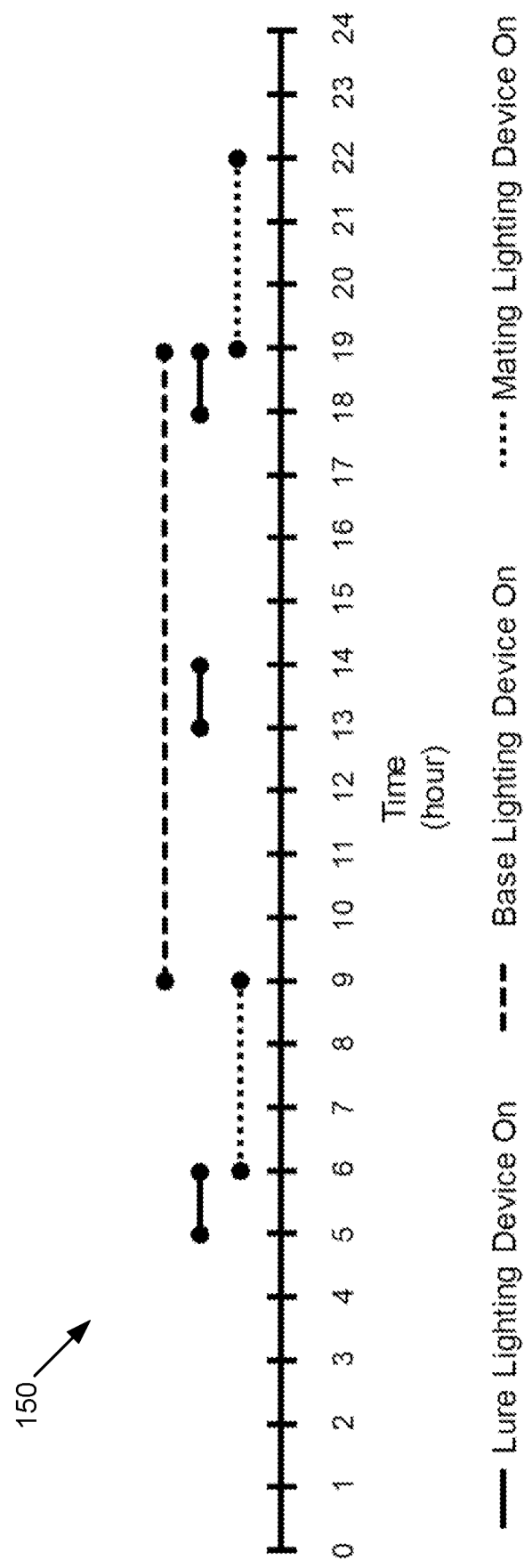
FIG. 4 is a diagram of an example lighting schedule that may be automated by a controller of the apparatus shown in FIG. 1 or 2.

Referring to FIG. 4, illustrated therein is a diagram 150 of an example lighting schedule that may be stored in memory 140 and/or the secondary storage 142 of controller 126 for automating operation of lure, mating and base lighting devices 104, 106 and 122. As shown, lure lighting device 104 is on from 05:00 to 06:00, 13:00 to 14:00, and 18:00 to 19:00; mating lighting device 106 is on from 06:00 to 09:00 and 19:00 to 22:00; and base lighting device 122 is on from 09:00 to 19:00. It will be appreciated that the example lighting schedule shown in FIG. 4 is one of many potential lighting schedules. The lighting schedule may be modified as desired. For example, each of the times noted above may be shifted forward or backward by an hour, 2 hours, 4 hours, etc. Alternatively, or in addition, the duration for which each lighting device is active (i.e., turned on) may be increased or decreased by 30 minutes, 60 minutes, 2 hours, etc.

In at least one embodiment, controller 126 may also be capable of opening and closing one or more lure ports 116. As described above, lure ports 116 may be closed to prevent stray light from passing into interior cartridge space 114 of pupae cartridge enclosure 112. Lure ports 116 may be opened and closed to coincide with when lure lighting device 104 is turned on and off, respectively. For example, according to the lighting schedule shown in FIG. 4, lure ports 116 may be opened at 5:00 and then closed at 6:00; opened at 13:00 and then closed at 14:00; and opened at 18:00 and then closed at 19:00.

Returning to FIG. 3, controller 126 may include an input device 144 for entering information and making requests. For example, input device 144 may be a keyboard, a keypad, a cursor-control device, a touchscreen, a camera, a microphone, or any combination of these. Input device 144 may be used to modify and/or replace the existing lighting schedule stored in memory 140 and/or secondary storage 142 of controller 126. In some cases, input device 144 may be used to select from two or more lighting schedules that are stored in memory 140 and/or secondary storage 142 of controller 126. Alternatively, input device 144 may be used to manually turn any one of the lure, mating and base lighting devices 104, 106 and 122 on or off. For example, one or more operators may use input device 144 of controller 126 to turn each of the lure, mating and base lighting devices 104, 106 and 122 on and off as desired.

Controller 126 may further include a display device 146 having a display screen for presenting visual information. For example, display device 146 may be a computer monitor, a flat-screen display, a projector, a display panel or any combination of these.

In the example shown, system 200 also includes an optional remote storage device 148 (e.g., cloud storage). Controller 126 may be configured to transmit data to storage device 148 across network 136. This data may include, for example, a log of which lighting devices are on at which times, a maintenance log, and/or an error log. Storage device 148 can store data received from controller 126. In some cases, storage device 148 may include one or more storage devices located at a networked cloud storage provider.

In at least one embodiment, the logging software may be stored in and retrieved from storage device 148 over network 136 (as opposed to being stored in memory 140 and/or secondary storage 142 of controller 126). Having the lighting schedules stored in storage device 148 may be convenient when multiple controllers 126 are used. In at least one embodiment, storage device 148 may store a plurality of preset lighting schedules of which to select (e.g., 25 or more lighting schedules). In such embodiments, memory 140 and/or secondary storage 142 may not offer enough storage for the plurality of lighting schedules.

Network 136 may be any communication network capable of carrying data, including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, Bluetooth®, and others, including any combination of these, capable of interfacing with, and enabling communication between, i) controller 126 and memory 138 and/or ii) controller 126 and each of the lure, mating and base lighting devices 104, 106 and 122.

Figure 5:
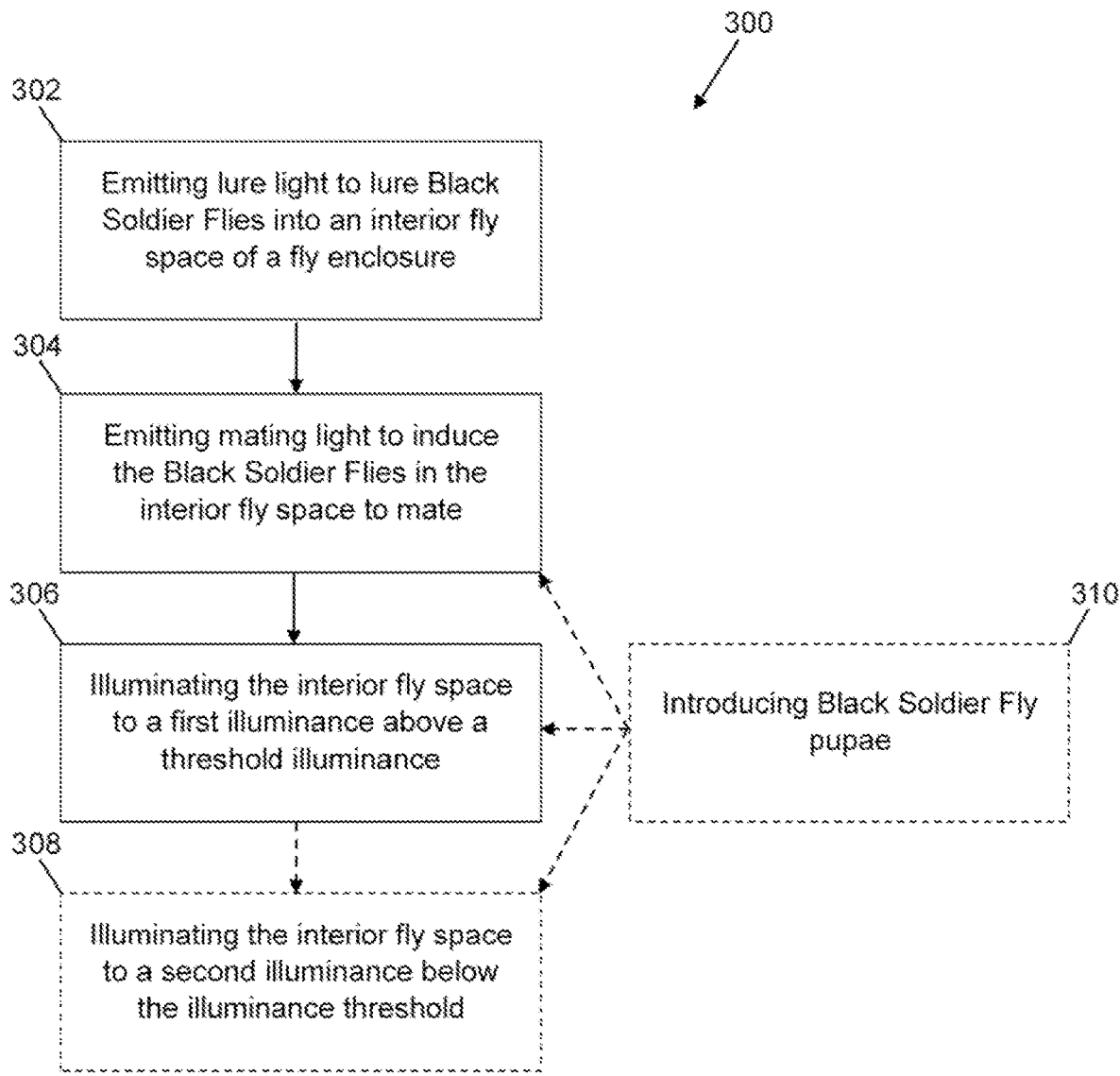
FIG. 5 is a flowchart of an example embodiment of a method of breeding Black Soldier Flies.

Referring now to FIG. 5, illustrated therein is a flowchart of an example embodiment of a Black Soldier Fly breeding method 300. Method 300 may be used to improve the yield of Black Soldier Fly eggs from a continuous population of Black Soldier Flies. As will be described in more detail below, method 300 may improve the yield of Black Soldier Fly eggs through an interchange of lighting periods that encourage the Black Soldier Flies to exhibit different behaviour. With all else being equal, by increasing egg production, greater quantities of Black Soldier Fly larvae may be reared, and ultimately harvested, for use as a source of protein. For clarity of illustration, method 300 is described below with reference to apparatus 100 shown in FIG. 1. However, method 300 is not limited to the use of apparatus 100 and can be practiced using any suitable apparatus.

At step 302, method 300 includes emitting a first light (lure light 118) to lure Black Soldier Flies into fly enclosure 102. As described above, lure light 118 has a first wavelength range that attracts the Black Soldier Flies. The first wavelength range may have a lower limit of about 280 nanometers and an upper limit of about 400 nanometers. For example, more preferably, the first wavelength range may be substantially between about 350 and about 400 nanometers. Light within such a wavelength range has been shown to effectively attract Black Soldier Flies even at low intensities (e.g., less than 10 lux).

At step 302, lure light 118 may be emitted so that it is visible from outside fly enclosure 102 through one or more lure ports 116. The emission of lure light 118 may lure Black Soldier Flies, which have recently hatched from pupae stage, into fly enclosure 102. As described above, when sufficient lure light is visible through lure ports 116, lure light 118 may provide a strong luring effect to encourage migration. For example, as shown in FIGS. 1 and 2, lure lighting device 104 may be in direct line of sight through lure ports 116. Such an arrangement may ensure a high proportion of lure light 118 is directed toward lure ports 116. Lure light 118 may be emitted at step 302 for a luring period that lasts about 30 to 90 minutes (lure lighting device 104 may be activated for this duration). The duration for which lure light 118 is emitted at step 302 may be altered to draw more or less adult Black Soldier Flies into fly enclosure 102.

At step 304, method 300 also includes emitting a second light (mating light 120) to induce the Black Soldier Flies in interior space 108 to mate. As describe above, mating light 120 has a second wavelength range that induces Black Soldier Flies to mate. A low level of broad-spectrum visible light with augmentation in the red and blue regions has been found proficient at inducing mating between Black Soldier Flies. The second wavelength range may have a lower limit of about 380 nanometers and an upper limit of about 740 nanometers. For example, more preferably, the second wavelength range may be substantially between about 410 nanometers and about 730 nanometers. Mating light 120 may start to induce mating behaviour at or above an intensity of about 1500 lux within the interior space. However, all else being equal, the higher the intensity of mating light 120, the greater its effect to induce mating. For example, mating light 120 at or above about 30,000 lux has shown a proficiency to induce mating. Accordingly, at step 304, it may be preferable to illuminate as much of interior space 108 as possible with mating light 120 of the highest possible intensity (up until 120,000 lux) while not inhibiting mating during this period. For example, exposing Black Soldier Flies to mating light 120 with an intensity above 120,000 lux may have an inhibitory effect on mating.

Mating light 120 may be emitted at step 304 for a mating period that lasts about 2 to about 4 hours (mating lighting device 108 may be activated for this duration). For example, more preferably, mating light 120 may be emitted at step 304 for a mating period of approximately 3 hours.

At step 304, one or more contrast panels (e.g., contrast panel $128_1$ and $128_2$ shown in FIGS. 1 and 2) may be provided to facilitate mating. Preferably, contrast panels 128 are light in color and/or translucent and located at or near the top of fly enclosure 102 to mimic a bright sky. As described above, providing a contrast panel 128 may help male Black Soldier Flies see and engage female Black Soldier Flies flying overhead.

At step 306, method 300 also includes illuminating interior space 108 of fly enclosure 102 to an illuminance above an illuminance threshold for an ovipositing period. In order to illuminate interior space 108 to an illuminance above the illuminance threshold at step 306, base light 124 may be provided by base lighting device 122, sunlight, or a combination thereof.

In at least one embodiment, the illuminance threshold may be about 1 lux. Alternatively, the illuminance threshold may be about 2-6 lux, or more. As described above, the illuminance threshold may be characterized as an illuminance level below which gravid Black Soldier Flies may become inactive. When a gravid Black Soldier Fly is inactive, it may not oviposit eggs. Accordingly, by keeping fly enclosure 102 illuminated above the illuminance threshold at step 306, gravid Black Soldier Flies may be prevented from becoming inactive. In addition, the provision of base light 124 at step 306 may help gravid Black Soldier Flies find ovipositing sites (e.g., egg-laying region 110 shown in FIGS. 1 and 2) and/or operators more easily navigate the area surrounding apparatus 100 (e.g., for maintenance or inspection purposes).

At step 306, it may be preferable to illuminate interior space 108 to an illuminance well above the illuminance threshold with base light 124. Providing such a margin or buffer may reduce (or even eliminate) the number of Black Soldier Flies that become inactive when base light 124 is being provided. If Black Soldier Flies are observed to be inactive during the ovipositing period at step 306, then the intensity of base light 124 can be increased to increase the illuminance of interior space 108. For example, the illuminance of interior space 108 may be increased by increasing the intensity of base light 124 that is emitted at step 306, repositioning the one or more base lighting devices 122, moving apparatus 100 closer to window(s) and/or providing additional base lighting devices 122. However, if the illuminance of interior space 108 is too high (above 1500 lux) during the ovipositing period at step 306, mating behaviour may be induced. It may be preferable to discourage mating behaviour from the ovipositing period at step 306 to increase overall egg production from method 300. Accordingly, at step 306, base light 124 preferably illuminates interior space 108 to an illuminance anywhere above the illuminance threshold (e.g., about 2-6 lux) and below about 1500 lux.

The ovipositing period at step 306 may last for about 6 to 12 hours. In at least one embodiment, one or more spaced apart luring periods at step 302 may occur during the ovipositing period at step 306 (e.g., see FIG. 4). Alternatively, or in addition, the ovipositing period at step 306 may at least partially overlap a portion of the luring period at step 302.

At step 308, method 300 may also include reducing illuminance of interior space 108 of fly enclosure 102 to an illuminance below the illuminance threshold for an inactive period. Accordingly, the inactive period at step 308 and the ovipositing period at step 306 may not overlap. Reducing the illuminance of interior space 108 below the illuminance threshold may be accomplished by turning lure, mating, and base lighting devices 104, 106 and 122 off. In at least one embodiment, the inactive period at step 308 may be scheduled to overlap with nighttime (e.g., sunset to sunrise).

During the inactive period at step 308, Black Soldier Flies within fly enclosure 102 may rest and conserve energy. Like many other animals, Black Soldier Flies have a biological sleep/wake cycle. Therefore, from a health perspective, it may be important to provide the Black Soldier Flies with such an inactive period at step 308. For example, the inactive period may last for about 6 to 16 hours and, more preferably, about 6 to 12 hours. Furthermore, in at least one embodiment, a luring period at step 302 may follow the inactive period at step 308. In at least one embodiment, a mating period at step 304 may follow the inactive period at step 308.

At step 310, method 300 may also include introducing at least one pupae cartridge (e.g., pupae cartridge 134 shown in FIGS. 1 and 2) so that it is in communication with interior space 108 of fly enclosure 102. As described above, each pupae cartridge 134 may hold a plurality of Black Soldier Fly pupae therein. The Black Soldier Flies lured into fly enclosure 102 at step 302 are adult Black Soldier Flies that have hatched from the plurality of Black Soldier Fly pupae.

At step 310, pupae cartridge 134 may be introduced or added during one of the mating period at step 304 and the ovipositing period at step 306. This may be convenient since sufficient light will be available for an operator to make such an introduction. Alternatively, pupae cartridge 134 may be introduced during another suitable time, e.g., during the inactive period at step 308. In this case, the operator may use a flashlight and/or night vision goggles to introduce the pupae cartridge. Pupae cartridge 134 may be kept in communication with interior space 108 of fly enclosure 102 for a hatching period of about 7 to 12 days. Removing a pupae cartridge 134 prematurely may reduce efficiency since not all of its pupae may have hatched yet. That is, late hatching pupae may not have a chance to enter fly enclosure 102 and ultimately mate.

Figure 6:
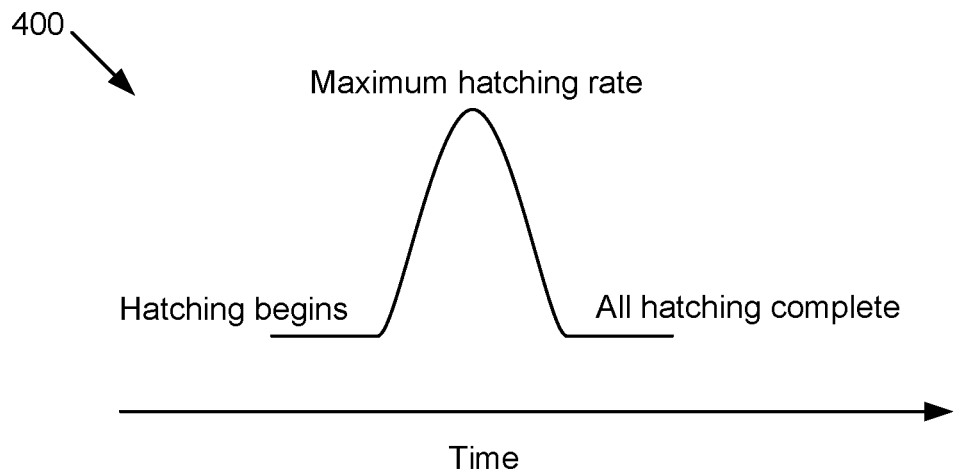
FIG. 6 is an example plot of Black Soldier Fly hatching over time from a single pupae cartridge.

Referring to FIG. 6, illustrated therein is an example plot 400 of Black Soldier Fly hatching over time from a single pupae cartridge. As shown, hatching from a pupae cartridge may follow a Gaussian (or normal) distribution, reaching a maximum rate at a midpoint. Accordingly, when only one pupae cartridge is in communication with interior space 108 of fly enclosure 102, the number of Black Soldier Flies lured into interior space 108 at step 302 may follow a similar distribution. That is, there may be relatively small loading rate on both ends of the distribution (i.e., at the tales). When a fresh pupae cartridge is not introduced until the hatching rate of the previous pupae cartridge has petered out, the age distribution of Black Soldier Flies within the fly enclosure may mimic a series of sequential Gaussian distribution similar to hatching rates (FIG. 6). Such an introduction schedule may create cohorts or clusters of Black Soldier Flies at different ages. This generally leads to inconsistent egg production (i.e., there may be periods of higher production followed by periods of lower production).

Preferably, the number of Black Soldier Flies that are lured into interior space 108 of fly enclosure 102 at step 302 is kept at a relatively high and consistent level. This may provide for one or more advantages. For example, with a steady stream of adult Black Soldier Flies entering fly enclosure 102 at step 302, a higher number of Black Soldier Flies may be available to mate during the mating period at step 304. For at least this reason, it may be beneficial to introduce multiple pupae cartridges separated at specific time intervals, an example of which is shown in FIG. 7.

Figure 7:
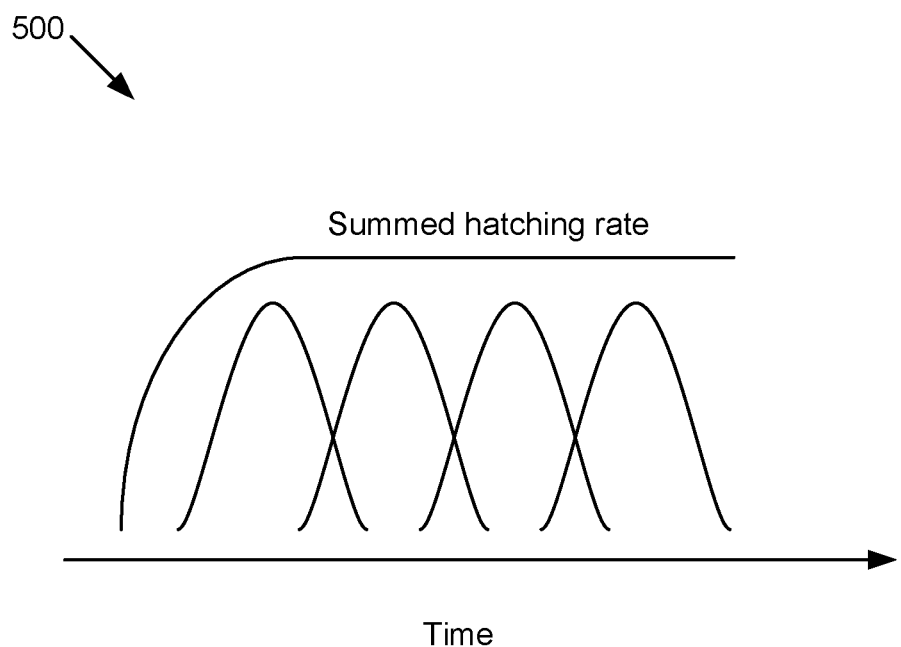
FIG. 7 is an example plot of Black Soldier Fly hatching over time from multiple pupae cartridges separated by a time interval.

Referring to FIG. 7, illustrated therein is an example plot 500 of Black Soldier Fly hatching over time from four pupae cartridges separated by a time interval. By adding pupae cartridges at intervals, the Gaussian hatching distributions of adjacent pupae cartridges may be timed to overlap with each other. As shown, this may have the effect of smoothing the emergence of the new Black Soldier Flies. Effectively, hatchings in one pupae cartridge are petering out as hatchings in an adjacent one are ramping up. The smoothness of the summed hatching rate may be varied by adjusting (i.e., increasing or decreasing) the interval at which new pupae cartridges are loaded. For example, decreasing the interval may increase the smoothness of the summed hatching rate. More specifically, decreasing the time interval between introductions of new pupae cartridges may reduce fluctuations in the Black Soldier Fly population within fly enclosure 102.

As shown by comparison of FIG. 7 to FIG. 6, when a plurality of pupae cartridges are introduced and separated by a time interval, the hatching rate may be kept at a consistent and elevated level. It follows that introducing multiple pupae cartridges separated by an interval may sustain the density of Black Soldier Flies within the fly enclosure at a consistent and elevated level. Furthermore, this may maintain a smooth age distribution of a Black Soldier Flies within the fly enclosure (i.e., there is generally an equal amount of Black Soldiers across each age). In turn, this leads to consistent and sustained levels of egg production. It will be appreciated that a consistent and sustained level of egg production may provide a Black Soldier Fly larvae rearing facility with the ability to streamline other related processes and operations, leading to a more efficient and economically viable production of Black Soldier Fly larvae on the whole.

As described above and shown in FIGS. 1 and 2, communication between fly enclosure 102 and pupae cartridges 134 may be provided by one or more lure ports 116. In at least one embodiment, at step 310, a pupae cartridge is introduced in communication with the fly enclosure through a corresponding lure port 116. As an example, if there are five lure ports, there may be five pupae cartridges in communication with the fly enclosure at a given time. As described above, each of the pupae cartridges 134 may be connected to a corresponding lure port 116 along with an optional frustoconical conduit 145.

Continuing with the example above, one of the five pupae cartridges may be replaced about every 2 days. This means that each of the five pupae cartridges may be in communication with fly enclosure 102 for a total of about 10 days. The time between the start of hatching and the end of hatching may vary between pupae cartridges. In some cases, it may be about 8 to 10 days. Accordingly, in this example, by keeping the pupae cartridges in communication with fly enclosure 102 for about 10 days, sufficient time may be provided for substantially all the Black Soldier Flies pupae held in that pupae cartridge to hatch before it is replaced. It will be appreciated that the number of pupae cartridges 134, the number of lure ports 116, and/or the rate of pupae cartridge replacement may each be adjusted as desired (e.g., to maximize loading rate, to lower labour cost, to reduce loss of unhatched pupae, and/or to streamline operation).

Returning to FIG. 5, the density of Black Soldier Flies within fly enclosure 102 may be important from a mating perspective. As described above, Black Soldier Flies have a courtship ritual that requires close proximity. A male Black Soldier Fly may identify a suitable female Black Soldier Fly with which to mate by observing the female flying above them (or below them). Accordingly, if the density of Black Soldier Flies is too low, mating rates during the mating period at step 306 may be suboptimal (i.e., not enough male Black Soldier Flies may identify mates). An approximate density of Black Soldier Flies may be tracked by eye. To determine a more precise density an optical capture system, such as a camera, may be used.

Egg production may be sustained at an elevated level when the Black Soldier Fly population is continuously kept between about 7,000 and about 40,000 flies per $m^3$ of fly enclosure. As described above, such high and continuous population of adult Black Soldier Flies may be supported by introducing pupae cartridges at a set interval (e.g., every 2 days) to provide a constant supply of newly hatched and ready to mate adults flies into interior space 108.

When the density of Black Soldier Flies within fly enclosure 102 drops below a predetermined density threshold, one or more cold stored pupae cartridges may be introduced in communication with interior space 108 of fly enclosure 102 at step 310 (e.g., connected to one or more of the lure ports 116). Similar to pupae cartridges 134 described above, a cold stored pupae cartridge also holds a plurality of Black Soldier Fly pupae therein. However, the pupae held within the cold stored pupae cartridge may hatch earlier as described below. For example, about 70 to 95% of the Black Soldier Fly pupae held in a cold stored pupae cartridge may hatch within about 2 to 3 days after introducing the pupae cartridge in communication with fly enclosure 102 (and sometimes sooner). Effectively, cold stored pupae cartridges may be used to provide interior space 108 of fly enclosure 102 with a quick inflow of adult Black Soldier Flies when density becomes too low.

To create a cold stored pupae cartridge, a pupae cartridge may be placed in cold storage with temperatures ranging from about 4 to 10° C. prior to its pupae hatching. By chilling the pupae cartridges (subjecting them to low temperatures), the pupae held therein may be placed into a state of stasis. One or more cold stored pupae cartridges may be removed from cold storage when needed.

Adult Black Soldier Flies have shown that they are ready to mate as soon as they enter interior space 108 of fly enclosure 102. Once newly hatched adults are lured into fly enclosure 102, mating light 120 of selected wavelengths, e.g., as described above, may be used to induce mating. Thus, from a mating efficiency perspective, it may be beneficial for the mating period at step 304 to follow the luring period at step 302. In at least one embodiment, the mating period at step 304 may immediately follow the luring period at step 302 (i.e., no gap in between).

The emission of mating light 120 at step 304 may discourage gravid Black Soldier Flies from laying eggs. For instance, the constant emission of mating light 120 for extended durations has been shown to be suboptimal. As described above, when Black Soldier Flies are subjected to mating light 120 for an extended duration, that mating light 120 may gradually lose its effectiveness to induce mating. Accordingly, it may be beneficial to provide gaps, before and after the mating period at step 304, in which gravid Black Soldier Flies may oviposit eggs (lay eggs). Therefore, it may be beneficial for the ovipositing period at step 306 to follow the mating period at step 304. In at least one embodiment, the ovipositing period at step 306 may immediately follow the mating period at step 304 (i.e., no gap in between). The transition between the mating period at step 304 and the ovipositing period at step 306 may also have the added benefit of subjecting the Black Soldier Flies to a contrast in light intensities, which may induce a change in behaviour.

While the above description describes features of example embodiments, it will be appreciated that some features and/or functions of the described embodiments are susceptible to modification without departing from the spirit and principles of operation of the described embodiments. For example, the various characteristics which are described by means of the represented embodiments or examples may be selectively combined with each other. Accordingly, what has been described above is intended to be illustrative of the claimed concept and non-limiting. It will be understood by persons skilled in the art that other variants and modifications may be made without departing from the scope of the claimed subject matter as defined in the claims appended hereto. The scope of the claims should not be limited by the preferred embodiments and examples, but should be given the broadest interpretation consistent with the description as a whole.

The invention claimed is:

1. An apparatus for breeding Black Soldier Flies, the apparatus comprising:
   a fly enclosure defining an interior fly space, the fly enclosure having an enclosure sidewall comprising at least one lure port in communication with the interior fly space;
   a pupae cartridge coupled to the at least one lure port on a first side of the enclosure sidewall;
   one or more lure lighting devices, each lure lighting device being operable to emit lure light having a first wavelength range that attracts the Black Soldier Flies, wherein each lure lighting device is spaced apart from the enclosure sidewall on a second side thereof, opposite the first side, so that the lure light emitted by that lure lighting device is visible through the at least one lure port to draw the Black Soldier Flies from the pupae cartridge, through the at least one lure port and into the interior fly space, the first wavelength range having a lower limit of 280 nanometers and an upper limit of 400 nanometers; and
   one or more mating lighting devices, each mating lighting device being operable to emit mating light having a second wavelength range that induces the Black Soldier Flies in the interior fly space to mate, each mating lighting device being oriented so that the mating light emitted by that mate lighting device illuminates the interior fly space, the second wavelength range having a lower limit of 380 nanometers and an upper limit of 740 nanometers.

2. The apparatus of claim 1, further comprising one or more base lighting devices, each base lighting device being operable to emit a base light, each base lighting device being oriented so that a collective base light emitted by the one or more base lighting devices illuminates the interior fly space to an illuminance above an ovipositing illuminance threshold.

3. The apparatus of claim 2, wherein the illuminance is above the ovipositing illuminance threshold and below 1500 lux, and wherein the ovipositing illuminance threshold is between 1 lux to 6 lux.

4. The apparatus of claim 2, wherein each base lighting device is positioned outside and above the fly enclosure.

5. The apparatus of claim 1, wherein each lure lighting device is spaced 0.5 meters to 2.5 meters apart from the at least one lure port.

6. The apparatus of claim 1, wherein each lure lighting device is positioned within the fly enclosure, and wherein each mating lighting device is positioned outside and above the fly enclosure.

7. The apparatus of claim 1, further comprising one or more egg-laying regions located within the fly enclosure, and wherein each egg-laying region includes an egg block on which gravid Black Soldier Flies lay eggs and an attractant substance to attract the gravid Black Soldier Flies to the egg block.

8. The apparatus of claim 1, wherein the at least one lure port includes a frustoconical conduit connected thereto, the frustoconical conduit being adapted to allow for passage of hatched Black Soldier Flies from pupae cartridge into the interior fly space, while restricting passage of the Black Soldier Flies from the interior fly space to pupae cartridge.

9. The apparatus of claim 1, further comprising a pupae cartridge enclosure adjacent the fly enclosure, the pupae cartridge enclosure being structured to define an interior cartridge space, wherein the enclosure sidewall is a dividing wall that separates the interior fly space from the interior cartridge space.

10. The apparatus of claim 9, wherein the dividing wall is substantially impervious to light, and wherein the pupae cartridge enclosure is substantially impervious to light.

11. The apparatus of claim 1, wherein the fly enclosure has a bottom side that is funnel-shaped to collect deceased Black Soldier Flies under gravity, and wherein the fly enclosure has at least one access port to permit removal of deceased Black Soldier Flies from the interior fly space.

12. The apparatus of claim 1, further comprising one or more contrast panels, each contrast panel being positioned above the fly enclosure.

13. The apparatus of claim 1, further comprising a controller having at least one processor that is operable to receive program instructions from a memory device, the controller being coupled to one or more of (i) each lure lighting device and (ii) each mating lighting device so that when the at least one processor executes the program instructions the controller is configured to control the activation of at least one of the lure lighting devices and/or (ii) at least one of the mating lighting devices in an automated fashion.

14. The apparatus of claim 13, wherein the controller is configured to control one or more of (i) at least one of the lure lighting devices and/or (ii) at least one of the mating lighting devices according to a lighting schedule.

15. The apparatus of claim 13, wherein the controller is configured to activate at least one of the mating lighting devices for a mating period after a luring period for which at least one of the lure lighting devices is activated.

16. The apparatus of claim 15, wherein the controller is configured to activate: i) at least one of the lure lighting devices so that the luring period lasts for 30 minutes to 90 minutes, and/or ii) at least one of the mating lighting devices so that the mating period lasts for 2 hours to 4 hours.

17. The apparatus of claim 13, wherein the controller is configured to activate at least one of the mating lighting devices for a mating period during a later portion of a luring period for which at least one of the lure lighting devices is activated.

18. The apparatus of claim 13, further comprising one or more base lighting devices, each base lighting device being operable to emit a base light, each base lighting device being oriented so that a collective base light emitted by the one or more base lighting devices illuminates the interior fly space to an illuminance above an ovipositing illuminance threshold, wherein the controller is coupled to each of the base lighting devices so that when the at least one processor executes the program instructions the controller is configured to control the activation of at least one of the base lighting devices in an automated fashion, the controller being configured to activate at least one of the base lighting devices for an ovipositing period after the mating period for which at least one of the mating lighting devices is activated.

19. The apparatus of claim 18, wherein the controller is configured to activate at least one of the base lighting devices so that the ovipositing period lasts for 6 to 12 hours.

20. A method of breeding Black Soldier Flies, the method comprising:
emitting lure light to lure the Black Soldier Flies into an interior fly space of a fly enclosure, the lure light having a first wavelength range that attracts the Black Soldier Flies, the first wavelength range having a lower limit of 280 nanometers and an upper limit of 400 nanometers;
emitting mating light to induce the Black Soldier Flies in the interior fly space to mate, the mating light having a second wavelength range that induces the Black Soldier Flies to mate, wherein said emitting the mating light comprises illuminating the interior fly space to at least a mating inducing illuminance threshold, the second wavelength range having a lower limit of 380 nanometers and an upper limit of 740 nanometers, wherein said emitting the mating light comprises illuminating the interior fly space to at least a mating inducing illuminance threshold; and
after said emitting the mating light, illuminating the interior fly space to a first illuminance above an ovipositing illuminance threshold and below the mating inducing illuminance threshold, wherein the ovipositing illuminance threshold is 1 to 6 lux, and the mating inducing illuminance threshold is 1500 lux.

21. The method of claim 20, further comprising illuminating the interior fly space to a second illuminance below the ovipositing illuminance threshold so that the Black Soldier Flies in the interior fly space are encouraged to rest.

22. The method of claim 21, wherein the method comprises illuminating the interior fly space to the second illuminance for an inactive period of 6 hours to 12 hours.

23. The method of claim 20, further comprising introducing at least one pupae cartridge so that the at least one pupae cartridge is coupled with the interior fly space of the fly enclosure, the at least one pupae cartridge holding a plurality of Black Soldier Fly pupae, and wherein said emitting the lure light further comprises luring the Black Soldier Flies that have hatched from the plurality of Black Soldier Fly pupae into the interior fly space.

24. The method of claim 23, wherein there are a plurality of pupae cartridges, and said introducing the at least one pupae cartridge comprises replacing one of the plurality of pupae cartridges every 2 to 3 days.

25. The method of claim 23, wherein the at least one pupae cartridge is coupled with the interior fly space, at least in part, by one or more lure ports, and said emitting the lure light comprises emitting the lure light so that the lure light is visible through each lure port.

26. The method of claim 20, wherein the method comprises illuminating the interior fly space to the first illuminance for an ovipositing period of 6 hours to 12 hours.

27. The method of claim 20, wherein the method comprises emitting the lure light by activating one or more lure lighting devices, and emitting the mating light by activating one or more mating lighting devices.

28. The method of claim 27, wherein the method comprises using a controller having at least one processor to control activation of at least one of the lighting devices, wherein the controller operates according to a lighting schedule.

29. The method of claim 20, wherein said illuminating the interior fly space to the first illuminance comprises providing a base light by (i) activating one or more base lighting devices, (ii) allowing sunlight to enter the interior fly space, or (iii) a combination of (i) and (ii).

* * * * *